United States Patent
Siedle et al.

(10) Patent No.: US 6,323,151 B1
(45) Date of Patent: Nov. 27, 2001

(54) ELASTIC POLYPROPYLENES AND CATALYSTS FOR THEIR MANUFACTURE

(75) Inventors: Allen R. Siedle, Lake Elmo; David K. Misemer, Maplewood; Vasant V. Kolpe, Mendota Heights; Brook F. Duerr, Lake Elmo, all of MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/391,541

(22) Filed: Sep. 8, 1999

Related U.S. Application Data

(62) Division of application No. 08/956,880, filed on Oct. 23, 1997.

(51) Int. Cl.$^7$ ................................ B01J 30/38; C08F 4/16; C08F 10/06

(52) U.S. Cl. ................ 502/152; 502/104; 502/117; 526/127; 526/160; 526/943; 526/351; 556/11; 556/12; 556/53

(58) Field of Search ................. 526/127, 160, 526/943, 351; 502/104, 152, 117; 556/11, 12, 53

(56) References Cited

U.S. PATENT DOCUMENTS

| | | | |
|---|---|---|---|
| 2,732,398 | 1/1956 | Brice et al. | 260/503 |
| 3,051,690 | 8/1962 | Vandenberg | 260/88.2 |
| 3,175,999 | 3/1965 | Natta et al. | 260/93.7 |
| 3,258,455 | 6/1966 | Natta et al. | 260/93.7 |
| 3,305,538 | 2/1967 | Natta et al. | 260/93.7 |
| 3,364,190 | 1/1968 | Emrick | 260/93.7 |
| 4,335,225 | 6/1982 | Collette et al. | 525/240 |
| 4,752,597 | 6/1988 | Turner | 502/104 |
| 4,769,510 | 9/1988 | Kaminsky et al. | 585/512 |
| 4,791,180 | 12/1988 | Turner . | |
| 4,794,096 | 12/1988 | Ewen | 502/117 |
| 4,892,851 | 1/1990 | Ewen et al. | 502/104 |
| 4,975,403 | 12/1990 | Ewen | 502/113 |
| 5,026,798 | 6/1991 | Canich | 526/127 |
| 5,132,381 | 7/1992 | Winter et al. . | |
| 5,155,080 | 10/1992 | Elder et al. | 502/152 |
| 5,198,401 | 3/1993 | Turner et al. . | |
| 5,225,500 | 7/1993 | Elder et al. | 526/127 |
| 5,281,679 | 1/1994 | Jejelowo et al. . | |
| 5,324,800 | 6/1994 | Welborn et al. | 556/160 |
| 5,347,026 | 9/1994 | Patsidia et al. . | |
| 5,391,789 | 2/1995 | Rohrmann | 556/11 |
| 5,393,911 | 2/1995 | Patsidia et al. . | |
| 5,401,817 | 3/1995 | Palackal et al. . | |
| 5,406,013 | 4/1995 | Patsidis et al. . | |
| 5,436,305 | 7/1995 | Alt et al. | 526/160 |
| 5,459,117 * | 10/1995 | Ewen | 502/117 |
| 5,459,218 | 10/1995 | Palackal | 526/351 |
| 5,516,848 | 5/1996 | Canich et al. | 525/240 |
| 5,539,056 | 7/1996 | Yang et al. | 525/240 |
| 5,594,080 | 1/1997 | Waymouth et al. | 526/126 |
| 5,596,052 | 1/1997 | Resconi et al. | 526/127 |
| 5,668,230 | 9/1997 | Schertl | 526/160 |
| 5,672,668 | 9/1997 | Winter et al. . | |
| 5,726,264 | 3/1998 | Jung et al. | 526/170 |
| 5,786,495 | 7/1998 | Resconi et al. . | |

FOREIGN PATENT DOCUMENTS

| | | |
|---|---|---|
| 537130 | 4/1993 | (EP) . |
| 604908 | 7/1994 | (EP) . |
| 0 628 577 A2 | 12/1994 | (EP) . |
| 666267 | 8/1995 | (EP) . |
| 707016 | 4/1996 | (EP) . |
| 729984 | 9/1996 | (EP) . |
| 754698 | 1/1997 | (EP) . |
| 934281 | 8/1963 | (GB) . |
| WO 90/12816 | 11/1990 | (WO) . |

OTHER PUBLICATIONS

A. D. Horton, Metallocene Catalysis: Polymers by Design? Trends in Polymer Science, 2, No. 5, pp. 158–166, (1994).

Z. Xu, et al., Advances in Polymer Science, vol. 120, Springer–Verlag, Berlin Heidelberg (1995) pp. 1–50.

J. Brandrup et al., Polymer Handbook, 3d Edition, John Wiley & Sons, NY (1989) section V. p. 29.

Chien et al. J. Am. Chem. Soc., 112, 2030 (1990).

Ewen, et al., Catalytic Olefin Polymerization, T. Keii and K. Soga, eds., Elsevier (1990) pp. 439–482.

Llinas et al, Crystalline–Amorphous Block Polypropylene and Nonsymmetric ansa–Metallocene Catalyzed Polymerization, Macromolecules, 25, 1242–1253 (1992).

Lin et al, Dynamic Mechanical Measurement of Crystallization–Induced Gelation in Thermoplastic Elastomeric poly(propylene), Macromolecules, 24, 850–854 (1991).

Gauthier et al, Elastomeric Poly9propylene): Influence of Catalyst Structure and Polymerization Conditions on Polymer Structure and Properties, Macromolecules, 28, 3771–3778 (1995).

(List continued on next page.)

Primary Examiner—David W. Wu
Assistant Examiner—R. Harlan
(74) Attorney, Agent, or Firm—Lorraine R. Sherman; Philip Y. Dahl

(57) ABSTRACT

A propylene polymeric composition with elastic character that is soluble in at least one nonpolar organic solvent selected from the group consisting of toluene, xylene, heptane, and hexane, comprises greater than 3 weight percent and up to 45 weight percent homotactic sequences each having only r or m diads, all of which homotactic sequences have a helical length in the range of 20 to 150 Å, and in the range of 55 to 97 weight percent of the sum of homotactic sequences of less than 20 Å in helical length, each homotactic sequence having only r or m diads and having fewer than 10 repeat units with mmmm pentads being present in the range of 0 to 35 weight percent of the total composition, and heterotactic sequences having r and m diads of unequal number, the polymer having a molecular weight ($M_w$) of at least 70,000.

12 Claims, 6 Drawing Sheets

OTHER PUBLICATIONS

Rieger et al, Unsymmetric ansa–Zirconocene Complexes with Chiral Ethylene Bridges: Influence of Bridge Conformation and Monomer Concentration on the Stereoselectivity of the Propene Polymerization Reaction, Organometallics, 13, 647–653 (1994).

Stehling et al., ansa–Zirconocene polymerization Catalysts with Annelated Ring Ligands—Effects on Catalytic Activity and Polymer Chain Length, Organometallics, 13, 964–970 (1994).

Piemontesi et al, Crystal Structures and Solution Conformations of the Meso and Racemic Isomers of (Ethylenebis(l–indenyl)zirconium Dichloride, Organometallics, 14, 1256–1266 (1995).

Ready et al., Alkyl–substituted indenyl titanium precursors for syndiospecific Ziegler–Natta polymerization of styrene, Journal of Organometallic Chemistry, 519 (1996) 21–28.

Greifenstein et al., Response of Acidity and Magnetic Resonance Properties to Aryl Substitution in Carbon Acids and Derived Carbanions: 2– and 3– Arylindenes, J. Org. Chem., 46. 5125–5132 (1981).

Kaminsky W., Highly active metallocene catalysts for olefin polymerization, J. Chem. Soc., Dalton Trans., 1998, p. 1413–1418.

Britovsek et al., Novel olefin polymerization catalysts based on iron and cobalt, Chem. Commun., 1998, 849–850.

Small et al., Highly Active Iron and Cobalt Catalysts for the Polymerization of Ethylene, J. Am. Chem. Soc., 1998, 120, 4049–4050.

Abstrats of Papers, Part 2, $215^{th}$ ACS National Meeting 8412–3557–0, American Chemical Society, Dallas, TX, Mar. 29–Apr. 2, 1998.

* cited by examiner

Comparative

Comparative

ELASTIC POLYPROPYLENES AND CATALYSTS FOR THEIR MANUFACTURE

This application is a divisional of U.S. Ser. No. 08/956,880 filed Oct. 23, 1997.

FIELD OF THE INVENTION

This invention relates to a novel class of polypropylenes that possess elastic character and are hybrid polymers having stereregularity intermediate between those that are highly syndiotactic (or highly isotactic) and those that are atactic, as well as catalysts that produce these hybrid polymers.

BACKGROUND OF THE INVENTION

Elastic polypropylene was first isolated by solvent extraction of polypropylene obtained by Ziegler-Natta polymerization of propylene (inter alia, U.S. Pat. No. 3,175,999). A process for preparing primarily isotactic, fractionable, elastomeric polyolefins has been described (U.S. Pat. No. 4,335,225), using a catalyst prepared by reacting a solid support such as alumina with, e.g., a tetraalkylzirconium compound. U.S. Pat. No. 5,594,080 discloses preparation of a stereoblock elastomeric polypropylene using a metallocene catalyst containing two unbridged phenylindenyil liganids connected to zirconium , i.e. (phenylindenyl)$_2$ZrCl$_2$. Chien et al. (*J. Am. Chem. Soc.*, 112, 2030 (1 990); *macromolecules*, 25, 1242 (1992); *macromolecules*, 24, 850 (1991)) prepared a thermoplastic, elastomeric polypropylene containing about 30% crystalline isotactic polypropylene, using a metallocene catalyst.

Collins et al. (*Macromolecules*, 28, 3771 (1995); *Macromol. Symp.*, 98, 223 (1995)) describe the use of zirconium and hafnium metallocene catalysts to prepare elastic polypropylene. These polymers had 29–54% mmmm pentads, i.e. they were predominantly isotactic. Significantly, elastic polypropylene could only be obtained when the molecular weight was greater than 50,000 and when the mmmm content of the polymer exceeded 38%, using exclusively hafnium complexes.

European Patent Application No. 666,267 describes the use of a metallocene catalyst of the type {fluorenyl-C$_2$H$_4$-indenyl}ZrCl$_2$ to prepare polypropylene in the presence of hydrogen. Polymer properties are not described. The same catalyst was used (*Organometallics*, 13, 647 (1 994)) to polymerize propylene in toluene in the absence of hydrogen; highly isotactic polymers having mmmm contents ranging from 38 to 64% and melting points of 104–110° C. were obtained. When the C$_2$H$_4$ bridging group was replaced by —SiMe$_2$— (U.S. Pat. No. 5,391,789), only a viscous, tacky oil was obtained.

European Patent Application No. EP 707,016 describes a catalyst system comprising {2-Me-4-naphthyl-indenyl-SiMe$_2$-fluorenyl}ZrCl$_2$, a Lewis acid compound and an organoaluminum compound, to prepare elastomeric polypropylene. U.S. Pat. No. 5,516,848 describes a process for making elastomeric polypropylenes employing a mixture of two different metallocene catalysts, one of which was a monocyclopentadienyl transition metal compound.

Metallocene catalysts generally can be defined as catalysts comprising one or more cyclopentadienyl groups, including substituted cyclopentadienyl groups, in combination with a transition metal, typically a metal of Group IVB of the Periodic Chart (i.e., titanium, zirconium, and hafnium). Useful metallocenes have been described comprising two cyclopentadienyl-type rings, in which both rings are identical (symmetrical metallocenes) and in which the two rings are different, due either to differing substitution patterns on identical ring systems or to the presence of two different ring systems (unsymmetrical metallocenes). The first reports of the use of cyclopentadienyl metallocenes to catalyze the polymerization of I-olefins appeared in 1957. British Patent Application GB 934,281 first described metallocene catalysts of the type (R-indenyl)$_2$MX$_2$ and (R-fluorenyl)$_2$MX$_2$, where R represents an alkyl or aryl substitLutent on the aroniatic ring, M represents titaniiumi zirconium or hafnium, and X represents a halide or an alkyl or alkoxy group, or the like, having from 1 to 12 carbon atoms. Since then, numerous patents and other publications have provided ample evidence of the commercial interest in these materials.

Four limiting cases illustrate the possibilities for stereoregularity in polypropylene. The isotactic structure is typically described as having the methyl side groups oriented so that they are all on the same side of the plane containing the polymer backbone. Another way of describing the isotactic structure employs Bovey's NMR (nuclear magnetic resonance) nomenclature: An isotactic diad, represented by m (for meso), is a pair of propylene units placed in the polymer chain so that both methyl side groups lie on the same side of the plane containing the polymer backbone. Similarly, a mmrnrn pentad represents five monomel units with their methyl groups all oriented the same way. $^{13}$C NMR can be used to determine the relative amounts of the various pentads present in a propylene polymer.

In contrast, in the syndiotactic structure, the methyl groups are oriented alternately above and below the plane containing the polymer backbone. A pair of propylene units with this up-down arrangement comprises an r (for racemic) diad, and rrrr would correspond to five similarly arranged monomer units.

Hemi-isofactic polypropylene is similar to the isotactic kind except that every other methyl side group has a random orientation.

Finally, in the atactic polymer, the orientation of the methyl groups with respect to the plane containing the polymer backbone is random and the number of r and m diads is the same.

The physical properties of polypropylene depend greatly on polymer stereoregularity. For example, isotactic and syndiotactic polypropylene are crystalline polymers that are insoluble in hydrocarbon solvents such as cold xylene. Because of the presence of crystallites that scatter light, they are often opaque or translucent. Additionally, these polymers are stiff, inelastic, and high-melting, their melting points being 171 and 138° C., respectively.

In contrast, hemi-isotactic and atactic polymers are non-crystalline and soluble in cold xylene. Atactic polypropylene is transparent, flexible and elastomeric.

Because isotactic and syndiotactic polypropylenes are such useful materials, their preparation has been the object of extensive research. For example, catalysts that produce isotactic polypropylene are disclosed in U.S. Pat. Nos. 4,794,096 and 4,975,403; catalysts that lead to syndiotactic polyolefins are described in U.S. Pat. Nos. 3,258,455, 3,305, 538, 3,364,190, 4,892,851, 5,155,080 and 5,225,500.

The precise effect of changes in catalyst structure on catalyst activity and polymer stereoregularity is difficult to predict. For example, U.S. Pat. No. 5,459,218 describes catalysts of the type {flu-bridge-Cp}ZrCl$_2$, wherein flu=fluorenyl, bridge=Me$_2$Si or Ph$_2$Si, and wherein Me=methyl, Ph=phenyl, and Cp=cyclopentadienyl. It is broadly stated and claimed that the propylene polymers contain at least 50% rr content, whereas the syndiotactic content actually achieved ranged from 74 to 82%. The highest molecular weight given for the propylene polymers is 66,000. No unusual properties of these polymers were disclosed nor were any clues provided as to how the catalysts could be modified to produce polymers having a lesser or greater syndiotactic content. By comparison, U.S. Pat. No. 4,892,851 describes a catalyst of a very similar type, namely {flu—CMe$_2$—Cp}ZrCl$_2$, which is reported to produce even more highly syndiotactic (92% rr) polypropylene.

A relationship between catalyst symmetry and polypropylene stereostructure has been proposed (*Trends in Polymer Science*, 2, 158 (1994)). Symmetry elements, typically described in terms of "point groups" of a bis(fluorenyl) MX$_2$-type catalyst are shown in FIGS. 1 and 2 (comparative). FIG. 1 illustrates the different symmetry elements that can occur in metallocene catalysts and FIG. 2 provides illustrative examples. A catalyst (FIG. 1 and, e.g., FIG. 2 entry 20) having point group $C_{2v}$, has three symmetry elements: the structure is unchanged after a 180 degree rotation about the bisector of the MX$_2$ plane and there are two mirror planes of symmetry, reflections in which leave the structure unchanged. One contains the MX$_2$ plane $\sigma_h$ and the other is orthogonal to and bisects the MX$_2$ plane $\sigma_v$. Looking straight on at the MX$_2$ plane, one sees that the top and bottom as well as the left and right hand side of the catalyst molecule are the same. A catalyst 21 having point group $C_2$ (entry 21 in FIG. 2) contains only a $C_2$ axis: the top and bottom of the molecule are the same, so that 180 degree rotation about the bisector of the MX$_2$ plane leaves the structure unchanged. Catalyst 22 having point group $C_s$ contains only a mirror plane of symmetry orthogonal to and bisecting the MX$_2$ plane. Viewed as described above, the left- and right hand sides of the catalyst are the same but the top and bottom are different. Catalyst 25 of $C_1$ point group symmetry contain none of these three symmetry elements.

According to FIG. 2, catalysts of point group $C_{2v}$ are said to produce atactic polypropylene, except that Cp$_2$TiPh$_2$ (24) atypically produces a stereoblock isotactic polymer (perhaps by a different polymerization mechanism) at low temperatures. Metallocenes having $C_2$ and $C_s$ point group symmetry are said to produce isotactic and syndiotactic polymers, respectively. However, U.S. Pat. No. 4,769,510 describes catalysts of the type {ind-bridge-ind}MX$_2$, which exists in two isomeric forms. One form is chiral andic consists of a d,l pair of enantiomers; it produces isotactic polypropylene. The second (meso) form is achiral and produces atactic polypropylene (*Organometallics*, 14,1256(1995)). Catalysts with $C_1$ symmetry are said to produce either hemi-isotactic 23 (in FIG. 2) or stereoblock isotactic-atactic 25 (in FIG. 2) polypropylene.

European Patent Application No. 537,130 describes the effect of the size of an organic group attached to a cyclopentadietyl ring in metallocenes of tlhe type {Cp-CMe$_2$-flu}ZrCl$_2$ ($C_s$ point group symmetry), which was shown to produce syndiotactic polypropylene. Introduction of a methyl group into the 3-position of the cyclopentadienyl ring led to {3-MeCp-CMe$_2$-flu}ZrCl$_2$ ($C_1$ point group symmetry), which produced a hemi-isotactic polymer. When the 3-CH$_3$ group was replaced by a t-butyl group to form {3-t-BuCp-CMe$_2$-flu}ZrCl$_2$ (also $C_1$ point group), isotactic polypropylene was obtained instead.

U.S. Pat. No. 5,459,218 relates to syndiotactic polypropylene prepared using silyl bridged metallocenes and having molecular weights up to 66,000. U.S. Pat. No. 5,668,230 discloses certain specific ethylene bridged fluorenyl-containing metallocenes to catalyze olefins polymerization.

One skilled in the art can only conclude that there are no reliable, general correlations between the structure of a metallocene catalyst and the stereospecificity or the stereoregularity of polymers produced thereby.

SUMMARY OF THE INVENTION

Briefly, the present invention provides propylene homopolymers that are elastomeric and are soluble in at least one nonpolar organic solvent selected from the group consisting of toluene, xylene, heptane, and hexane, the polymer comprising
  a) greater than 3 weight percent and up to 45 weight percent of homotactic sequences, each having only r or m diads, all of which homotactic sequences have a helical length in the range of about 20 to 1 50 Å, and
  b) in the range of 55 to 97 weight percent of the total composition being the sum of
    1) homotactic sequences, each having only r or mn diads, and being less than 20 Å in helical length and having fewer than 10 repeat units with mmmm pentads being present in the range of 0 to 35 (preferably 0 to 31) weight percent of the total composition, and
    2) heterotactic sequences having unequal numbers of r and m diads,
the polymer having a weight average molecular weight ($M_w$) of at least about 70,000, preferably greater than 70,000 and up to 2,000,000, more preferably 75,000 to 1,000,000, and most preferably 80,000 to 500,000. The two b) components can be present in any amount so long as their sum amounts to 55 to 97 weight percent of the total composition.

The propylenes of the invention include homotactic sequences of length as specified above having all r or all m diads. As is appreciated by those skilled in the art, these homotactic sequences can assume a helical configuration. Connecting these homotactic sequences are similar hoinotactic sequences of less than 20 Å in helical length and having less than 10 repeat units as well as heterotactic sequences having both r and m diads present in unequal numbers. These polymers exhibit elastomeric character that varies from a stiff rubber to that of a very stretchy rubber band. The homotactic sequences can be all r or all m and preferably they are all r, i.e., syndiotactic. In general, the polymers comprise discontinuous small (20 Å to 150 Å in length) hard segments in a continuous softer matrix.

The length of the homotactic sequences can be estimated in the following way. Helical chains of polypropylene run approximately parallel to the c-axis of the unit cell of orthorhombic syndiotactic polypropylene. Four monomer units are contained in the unit cell which is 7.6 Å long. Therefore, each molecule of propylene contributes 7.6/4 or 1.9 Å to the chain length. This is a reasonable estimate because if the chain were fully extended, each propylene would contribute the distance of two C—C bonds or 3 Å to the chain length.

The heterotactic sequences comprise both r and m diads and are of variable lengths and are randomly dispersed as to size and distribution in the polymer chain.

Preferably, the propylene polymers of the invention also have one or more of the following characteristics:
  i) a stereoregularity index between 1.30 and 10.0, preferably 1.30 to 7.00 and more preferably 1.60 to 6.40.
  ii) a heat of fusion ($\Delta H_{fus}$) that is less than 50% of the $\Delta H_{fus}$ of 100% isotactic polypropylene when mm>rr; or less than 50% of the $\Delta H_{fus}$ of 100% syndiotactic polypropylene when rr>rnm, ($\Delta H_{fus}$ values are as given in J. Brandrup et al., POLYMER HANDBOOK, 3d Edition, John Wiley & Sons, NY (1989), section V, p. 29); and iii) optical clarity.

In another aspect, this invention provides blends of two or more different propylene polymers, at least one of which exhibits the properties described above. Blends of one or more propylene polymers as described above can further comprise crystalline or amorphous polypropylene, tackifying resins, antioxidants, fillers, and other adjuvants known in the art.

In yet another aspect, this invention provides copolymers of propylene wherein the propylene sequences are as defined above, and wherein the comonomers can be olefins having 2 to 20, preferably 2 to 8, carbon atoms. Copolymers can be blended with one another as well as with homopolymers which provides a way to tailor or modify polypropylene properties. Molecular weight of copolymers ($M_w$) can be in the range of 35,000 to 2,000,000, preferably 50,000 to 1,000,000, more preferably 70,000 to 500,000.

In a further aspect, this invention provides metallocene catalysts for propylene polymerization, having the structure {ligand1-bridge-ligand2}MX$_2$, wherein ligand1 and ligand2 are different and are selected from the group consisting of substituted and unsubstituted cyclopentadienyl (Cp), indenyl (ind), fluorenyl (flu), 4,5-dihydrocyclopentaphenanthryl (H$_2$CPA), and cyclopentaphenanthryl (CPA) ring groups, wherein, when present, ring group substituents can be selected from the group consisting of
i) $C_1$–$C_4$ straight-chain or branched alkyl,
ii) $C_6$–$C_{20}$ aryl,
iii) $C_7$–$C_{20}$ alkylaryl,
iv) $C_4$–$C_7$ cycloalkyl,
v) (—CH$_2$—)$_n$, wherein n is 2, 3, 4, or 5, or (—CH=CH—)$_m$ wherein mn is 1, 2, 3, or 4, connecting two positions (i.e., adjacent or non-adjacent ring carbon atoms) in the same ring structure, preferably the 4 and 5 positions in fluorenyl or indenyl,
vi) fused aromatic rings, and
vii) fused aromatic rings substituted by any one of groups i)-v);

bridge is a linking group joining ligand1 and ligand2 at C-1 of Cp or ind ligands or C-9 of flu and CPA ligands and is selected from the group consisting of
i)>CR$^1$R$^2$,
ii)>SiR$^1$R$^2$,
iii)—CR$^1$R$^2$—CR$^3$R$^4$—,
iv)—SiR$^1$R$^2$—SiR$^3$R$^4$—,
v)—CR$^1$R$^2$—SiR$^3$R$^4$—,
wherein R$^1$, R$^2$, R$^3$, and R$^4$ can be the same or different and are selected from the group consisting of H, $C_1$–$C_{20}$ straight-chain or branched alkyl groups, $C_6$–$C_{20}$ aryl groups, and $C_3$–$C_8$ cycloalkyl groups;

M is a metal atom selected from the group consisting of Zr, Hf, and Ti, preferably is zirconium or hafnium, and most preferably zirconium, and X is selected from the group consisting of Cl, Br, I, $C_1$–$C_{20}$ straight-chain or branched alkyl groups, $C_6$–$C_{20}$ aryl groups, $C_7$–$C_{20}$ alkaryl groups, and $C_7$–$C_{20}$ aralkyl groups, wherein the metallocene catalyst exhibits an asymmetry parameter ot 1.03 to 1.69, preferably 1.03 to 1.45, more preferably 1.05 to 1.35, with the proviso that the metallocene catalyst provides propylene polymers described above.

In a still further aspect, this invention also provides a method of making novel catalyst precursor compounds of the type H{ligand1 —CH$_2$CH$_2$— ligand2}H wherein ligand1 and ligand2 are as previously defined, the method comprising the steps:

1) deprotonating the hydroxyl group of a compound of the type ligand1—CH$_2$CH$_2$OH;

2) reacting the deprotonated compound with a perfluoro-alkylsulfonyl fluoride of the type R$_f$SO$_2$F to obtain a stable perfluoroalkylsulfonate of the type ligand1—CH$_2$CH$_2$—OSO$_2$R$_f$;

wherein R$_f$ means an alkyl group having 1–20 carbon atoms or an aryl group having 5 to 12 carbon atoms in which at least 75% of H atoms have been replaced by F atoms;

3) condensing the perfluoroalkylsulfonate with the conjugate base of a compound of the type ligand2-H;

wherein ligand1 and ligand2 are as previously defined and R$_f$ is independently selected from the group consisting of highly fluorinated or perfluorinated alkyl radicals containing from 1–20 carbon atoms.

In yet a further aspect, there is provided a novel class of metallocene catalysts that are particularly useful to prepare hybrid polymers of the present invention, i.e. those having intermediate stereoregularity between those that are highly syndiotatic (or highly isotactic) and those that are atactic, the novel catalysts of the present invention having the formula:

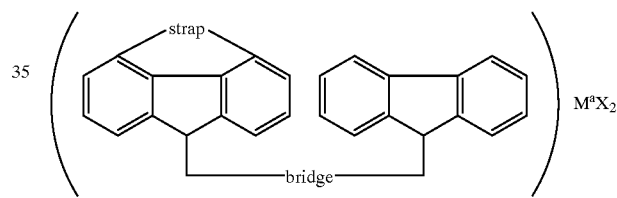

wherein
strap can be a (—CH$_2$—)$_n$ group or a (—CH=CH—)$_m$ group,
bridge is as previously defined,
M$^a$ is Zr or Hf,
n is 1, 2, 3, or 4 and m is 1, 2, 3, or 4, and
X is as previously defined,
with the proviso that when M$^a$=Zr, X=Cl, and bridge=C$_2$H$_4$, then strap can (—CH$_2$—)$_n$ or (—CH=CH—)$_m$, wherein n=3, 4 or 5, and m=2, 3, or 4, preferably m is 2, 3, or 4 and can be designated m'.

In yet another aspect, this invention also provides a method of controlling the stereostructure of polypropylene by choosing the shape of a metallocene catalyst, as defined by its asymmetry parameter, from the class of catalysts having the structure {ligand1-bridge-ligand2}MX$_2$, wherein
ligand1 and ligand2, bridge, M, and X are as previously defined, and wherein the metallocene catalyst exhibits an asymmetry parameter of 1.03 to 1.69, and the stereoregularity index of said polypropylene increases from about 1.30 to about 10.00 with an increase in the asymmetry parameter of the catalyst.

Preparation of the hybrid polypropylenes of the invention is accomplished by combining propylene with a metallocene catalyst, preferably in the absence of solvent for the monomer, in an inert atmosphere at a pressure in the range of 69 to 6890 Kpa at a temperature in the range of −20° C. to about 120° C. When a solvent is used, it can be a hydrocarbon, preferably aliphatic, cycloaliphatic, or aromatic, more preferably it is toluene or cyclohexane. Activation of the metallocene is accomplished by activators known in the art, preferably methylaluminoxane alone or in combination with trialkylaluminum compounds such as trimethylaluminum, triethylaluminum, or triisobutylaluminum.

As used herein:

"tasymmetry parameter (A.P.)" is defined as the ratio of the van der Waals surface area of the larger ligand to that of the smaller ligand, wherein the van der Waals surface area can be calculated by CAChe™ Satellite molecular modeling program (version 3.8) (Oxford Molecular Ltd., Oxford, United Kingdom) on a Macintosh computer; this is a measure of the asymmetric character of a molecule;

"atactic" means" polypropylene having no dominant tacticity and having 25% mm triads and 25% rr triads, as determined by NMR spectroscopy;

"Cp or cp" means cyclopentadienyl;

"CPA" means cyclopentaphenanthryl;

"elastomeric" or "elastic" means a material that at room temperature can be stretched repeatedly to at least twice its original length and, immediately upon release of the stress, returns with force to its approximate original length;

"entanglement molecular weight ($\overline{M}_e$)" means average molecular weight of chains between entanglements in a polymer;

"film" means a self-supporting layer;

"flu" means fluorenyl;

"group" or "radical" or "compound" or "ligand" or "monomer" or "polymer" means a chemical species that allows for substitution or which may be substituted by conventional substituents which do not interfere with the desired product; e.g., substituents can be alkyl, aryl, phenyl, etc.; andi "H$_2$CPA" means 4,5-dihydrocyclopentaphenanthryl;

"helical length" means the length of a segment in a coiled configuration in contrast to the fully extended polymer segment;

"heterotactic" sequences are those having both r or m diads;

"highly fluorinated" (R$_f$) means having at least 75% of H atoms in an alkyl cycloalkyl, or aryl group substituted by fluorine atoms;

"highly isotactic" means polypropylene having an mm content of at least 80%, as determined by NMR spectroscopy;

"highly syndiotactic" means polypropylene having an rr content of at least 80%, as determined by NMR spectroscopy;

"homotactic" sequences are those having diads which are all r or all m.

"ind" means indenyl;

"isotactic" or "isotactic-rich" means polypropylene having tacticity shown in FIG. 2 (second entry) and having an mm content of greater than the rr triad content, as determined by NMR spectroscopy;

"Me" means methyl;

"metallocene" means a metal-organic compound characterized by π-bonds between a transition metal and a cyclopentadienyl, indenyl, or fluorenyl ligand, or such substituted ligands;

"mm triads" refers to an isotactic structure having three propylene units placed in a polypropylene backbone such that all three methyl side groups lie on the same side of the plane containing the polymer backbone, as determined by NMR spectroscopy;

"mr triads" refers to a stereoregular polypropylene structure having three successive propylene units placed in a polypropylene backbone such that, relative to the first propylene unit, the methyl group of the second propylene lies on the same side of the plane containing the polymer backbone and the methyl group of the third propylene lies on the opposite side of the plane containing the polymer backbone, as determined by NMR spectroscopy;

"nanocystalline" means having crystallites in the nanometer size range (largest length), preferably 2 to 200 nm;

"optical clarity" means transmittance of greater than 80% of light of wavelengths of 400–750 nm;

"peak molecular weight," $M_p$, means the maximum molecular weight in a curve relating molecular weight and the abundance of a species of a given molecular weight determined by gel phase (or size exclusion) chromatography;

"Ph" means phenyl;

"rr triads" refers to a syndiotactic structure having three propylene units placed in a polypropylene backbone such that each successive methyl side group is alternately above and below the plane containing the polymer backbone, as determined by NMR spectroscopy;

"soluble" means dissolves to an extent of greater than 98 weight percent at a temperature up to the boiling point of the stated solvent;

"stereoregularity index (S.I.)" of a propylene polymer is defined as the ratio of the percentage of mm triads to rr triads, wherein the ratio represents the larger of mm or rr over the smaller of mm or rr (i.e., the ratio is positive and greater than 1); and "syndiotactic" or "syndiotactic-rich" means polypropylene having tacticity shown in FIG. 2 (third entry) and having an rr content of greater than the mm triad content, as determined by NMR spectroscopy.

Metallocene catalysts that produce highly isotactic or highly syndiotactic polymers exhibit a number of chemical and/or structural similarities:

1) These catalysts very often contain a MX$_2$ unit (M=Ti, Zr, or Hf; X=Cl, Br or CH$_3$, most commonly Cl) bonded to two variously substituted cyclopentadienyl-type ligands such as cyclopentadienyl itself, 1-indenyl or 9-fluorenyl.

2) The two cyclopentadienyl-type ligands may be connected by a bridging group joined at the C-1 position in the indenyl moiety or the C-9 position in the fluorenyl moiety. The groups —CH$_2$—CH$_2$— and —SiMe$_2$—, wherein Me=methyl, are common examples.

3) During the course of activation by an organoaluminum compound such as methylaluminoxane or mixtures of methylaluminoxane and other co-catalysts, Cl is replaced by one or two alkyl groups derived from the organoaluminum compound so that equivalent results for compounds containing a MCl$_2$ or M(Me$_2$) moiety are often seen.

4) Once a basic catalyst structural type that provides isotactic or syndiotactic polymer has been recognized, stereoregularity can be increased by further adjustments of the structure through introduction of organic groups on the cyclopentadienyl-type ligands.

However, prior to the present invention it was not possible to predict the physical properties of polypropylene of intermediate stereoregularity based on the shape of the metallocene catalyst.

Metallocene catalysts of the invention produce novel propylene polymers, herein sometimes referred to as hybrid polymers, whose stereoregularity lies between highly syndiotactic (or highly isotactic) and atactic. Polymers thus obtained exhibit novel and useful properties, for example resistance to creep at high temperatures or extreme extensibility, which properties have not been previously observed in polypropylene.

DETAILED DESCRIPTION OF THE INVENTION

Figure 1:
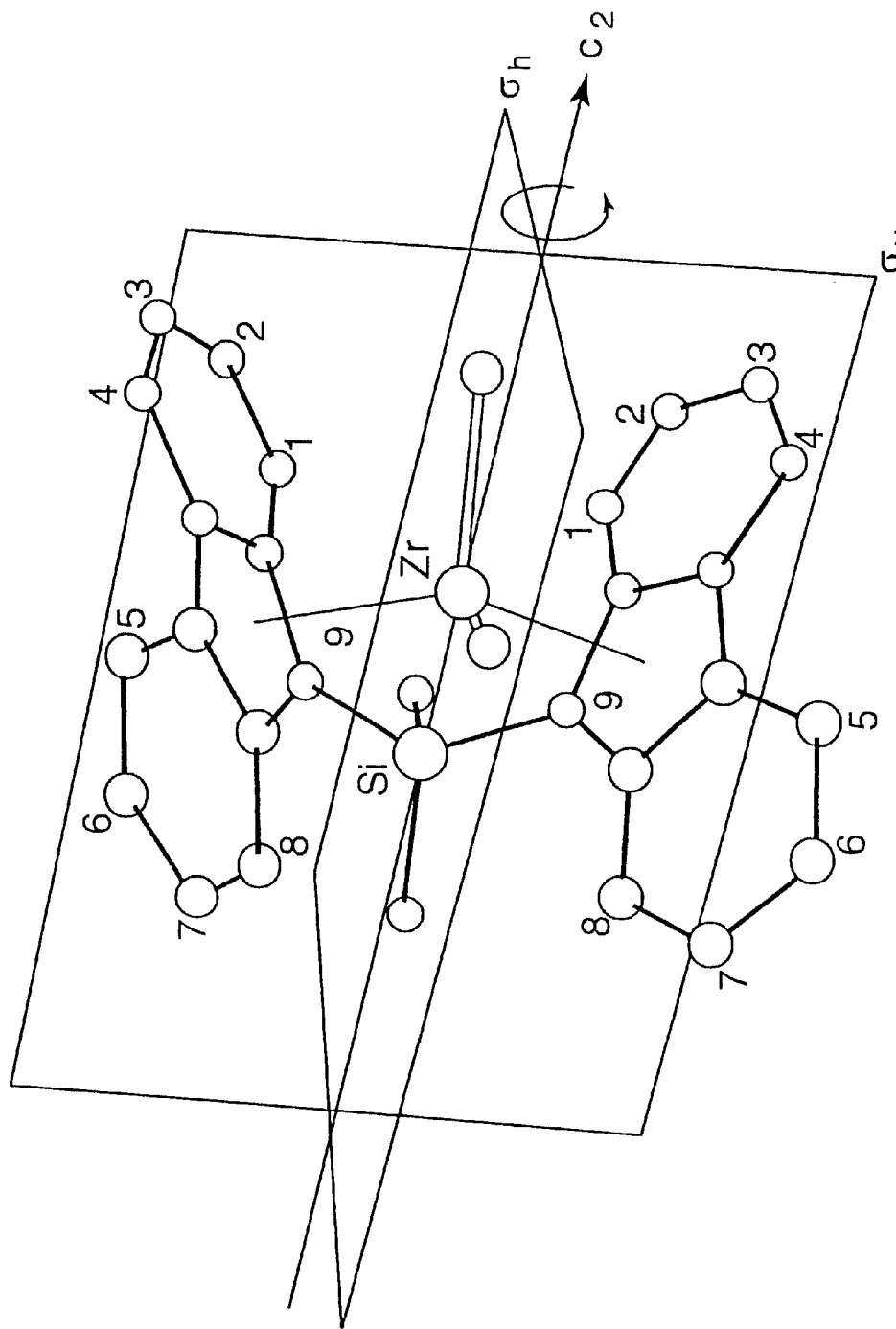
FIG. 1 shows the symmetry elements of an unsubstituted, bridged bisfluorenyl metallocene catalyst that is known in the art.
Figure 2:
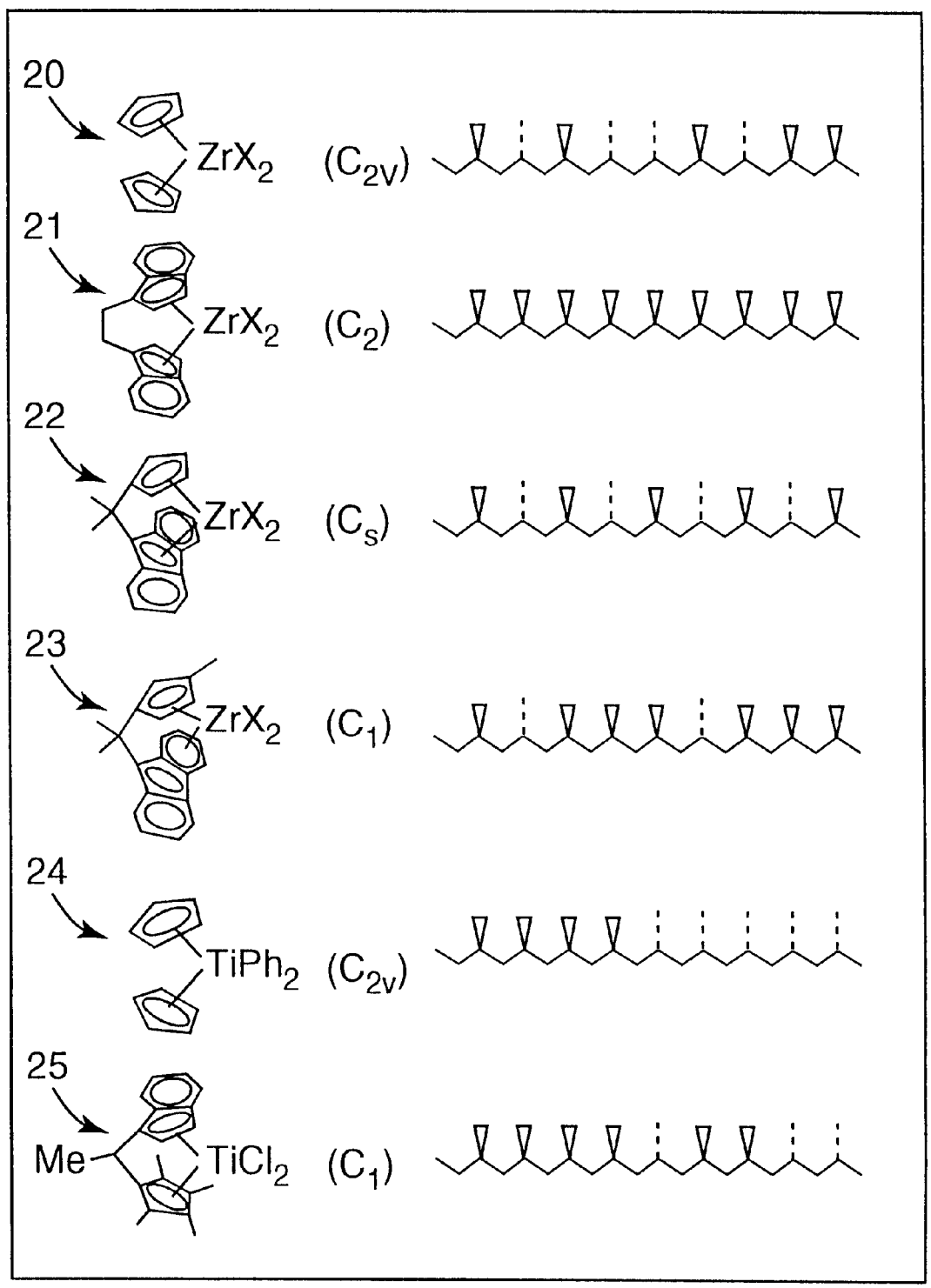
FIG. 2 shows the relationship between metallocene catalyst symmetry and polypropylene stereostructure for selected catalysts (20, 21, 22, 23, 24, 25) as is known in the art.

The present invention presents a simple, quantitative (numerical) means of describing the shape of metallocene catalysts, even those which have yet to be made. Using this simple metrical parameter, and noting the symmetry planes present in the structure of the catalyst molecule, it is possible to predict whether the catalyst will produce a highly isotactic polypropylene, one that is highly syndiotactic, or atactic. Polymers of the invention have properties that are not adequately described by any of the conventional designations, and may be referred herein as a hybrid polymer. The invention also presents a numerical measure of the stereoregularity of a poly(1-olefin).

As described above, propylene homopolymers can be divided according to their stereoregularity into three broad categories: isotactic, syndiotactic and atactic. The former two materials are crystalline, high melting, insoluble in (and resistant to) common organic solvents, stiff, tough and nontacky. They are particularly well suited to engineering applications where their high strength is beneficial.

These are, as has been mentionied limiting cases and they are describable in essentially statistical terms. Commercially available isotactic polypropylene can have an mm content of 90% or higher and commercial syndiotactic polypropylene can have an rr content of 70% or higher. Atactic polypropylene is not at present commercially available but descriptions of it in the art refer to tacky material in which the mm and rr content are each about 25%.

The present invention is directed toward preparation of novel propylene polymers whose mm (or rr) content exceeds 25% (which can be characterized as constituting a flexible, tacky polymer) to greater than 65% (where a high degree of structure can contribute significantly to the physical properties such as modulus and resistance to flow). Polymers of intermediate stereregularity can be hybrids, i.e. theiy can combine some of the properties of both highly crystalline and amorphous polymers, such as, for example, a material that is both tough and tacky.

In order to obtain such hybrid polymers, hybrid catalysts, intermediate in structure between those used to make highly isotactic (or highly syndiotactic) polypropylene and atactic polypropylene, are required. Unfortunately, as described above, the necessary features of such a hybrid catalyst have been difficult or impossible to identify by study of the art. What is needed, and provided by the present invention, are low symmetry catalysts (low A.P.) as well as a means of describing their shape, e.g., molecules that could not be adequately described by point group symmetry.

Metallocene catalysts in which two cyclopentadienyl-type ligands are connected by a bridging group are known. Such a bridge holds the two ligands in fixed positions relative to one another. Rotation of the ligands is prevented, substituents on the ligands are fixed in the molecular stricture, and the catalyst has, therefore, a permanent and definite shape.

When bridged metallocene catalysts are used, polymerization activity, i.e., joining an entering monomer molecule to the growing polymer chain, takes place in a very specific region of the metallocene catalyst molecule. For example, in a metallocene catalyst of the type (ligand)$_2$ZrCl$_2$, polymerization activity takes place around the —ZrCl$_2$ region. Numerous metallocene catalysts have been described having substituent groups at every conceivable free site of the ligand ring groups. However, many positions at which substituents could be introduced are so distant from the polymerization site (i.e., metal center) that substituents placed there have little or no effect on the stereochemical outcome of the polymerization. In the present invention, substituents located more than about 5 Å from the metal center aire ignored. For example, in fluorenyl ligands connected at C-9 to a bridge, substituents placed at the C-1, C-2, C-7 or C-8 ring positions are of essentially no stereochemical significance. In contrast, the C-4 and C-5 positions are quite close to the metal atom at which polymerization occurs so the size and nature of substituents located there are critical determinants of the catalyst's stereospecificity. Similarly, in bridged metallocenes containing a cyclopentadienyl-bridge-inidcnyl moiety (with the bridge being connected at C-1 of the indenyl ring group), substituents located at C-3 or C-4 in the cyclopentadienyl ligand; or at C-2, C-3, C-4, or C-5 in the indenyl ligand are considered of primary importance.

The numbering systems for cyclopentadienyl, indenyl, fluorenyl, and cyclopentaphenanthryl ligands are shown below:

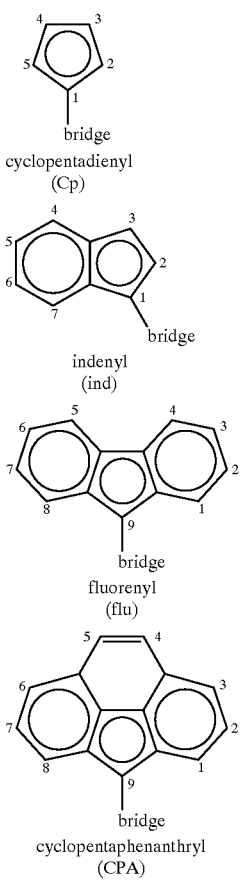

bridge
cyclopentadienyl
(Cp)

bridge
indenyl
(ind)

bridge
fluorenyl
(flu)

bridge
cyclopentaphenanthryl
(CPA)

Unsymmetrical bridged metallocene catalysts of the invention can be characterized by an asymmetry parameter (A.P.) as follows. For a metallocene catalyst of the type {ligand1-bridge-ligand2}MX$_2$, wherein M is selected from the group consisting of Ti, Zr, and Hf and each X is as previously defined, A.P. is the ratio area of the van der Waals surface of the larger ligand to that of the smaller, as determined by computer-assisted molecular modeling, such as, for example, the CAChe™ suite of programs from Oxford Molecular Inc. It is always continuous, positive and equal to or greater than 1. The surface areas of the ligand includes contributions from substituents at the critically important positions described above (i.e., those that are less than about 5 Å from the metal center). Substituents at other positions are ignored and hydrogen atoms are assumed to reside at those positions. The A.P. provides a numerical measure of the degree of asymmetry of a catalyst. The larger the value of A.P). for a metallocene, the more unsymmetrical it is. Sturface areas for the individual ligands are the areas comprising the constituent atoms at their van der Waals radii. They can be readily calculated using, e.g., the CAChe™ molecular modeling program. This program also permits placement of a substituent at a given position in an optimized geometry that minimizes non-bonded repulsions. For example, in calculating the surface area of a 3-phenylcyclopentadienyl ligand fragment, the five- and six-membered rings are not coplanar. The phenyl ring is allowed to rotate out of the plane of the cyclopentadienyl ring so as to reduce unfavorable steric interactions between hydrogen atoms. Several examples that illustrate how A.P. values are calculated follow.

A.P. for {flu-C$_2$H$_4$-flu}ZrCl$_2$ is 1.00 by definition because both ligands are the same. Because the bulky but distant t-butyl groups are ignored, it is 1.00 as well for the analogous {2,7-di-t-butyl-flu-C$_2$H$_4$-flu}ZrCl$_2$. Surface areas of fluorenyl and indenyl groups are calculated to be 151 and 112 square Angstroms, respectively. Therefore, A.P. for both of the catalysts {flu-C$_2$H$_4$-ind}ZrCl$_2$ and {flu-SiMe$_2$-ind}ZrCl$_2$ is 151/112, or 1.35.

We have found that one effective way of altering the shape (and A.P.) of catalysts is to connect the 4 and 5 positions of one of the fluorene rings by means of (—CH$_2$—)$_n$ or (—CH=CH—)$_m$, wherein n=2, 3, 4, or 5, and m=1, 2, 3, or 4, methylene or vinylene groups that are connected to one another so as to form a ring. Relative to an unsubstituted fluorene ring, these substituents increase the van der Waals surface areas thus making the substituted fluorene portion of the ligand larger and so increase the asymmetry parameter. In Table 2, these moieties are referred to as a STRAP. The two halves of the ligand molecule are connected with a BRIDGE which serves to inhibit rotation or movement of the different parts of the catalyst molecule and imparts to it a permanent and persistent shape.

Another effective means of providing asymmetrical catalysts is to use a ligand of the type flu-bridge-ind. This is related to the symmetrical flu-bridge-flu ligand by replacement of one (CH)$_4$ benzo rings by two hydrogen atoms. Again, the catalyst molecule has a persistent shape in contrast with asymmetrical, unbridged catalyst molecules. Unlike (ind(1)-bridge-ind(2))MCl$_2$ catalysts, wherein (1) and (2) indicate nonequivalent indenyl-type ligands and which exist as d,l and meso isomers (the former gives isotactic and the latter atactic polypropylene), such isomerism is not possible.

In order to correlate A.P. with stereoregularity, a numerical measure of stereoregularity, called the stereoreguzriay inldex, or S.I., is defined as follows: In a perfectly atactic polymer, the two homotactic triads, mm7 and rr, are present in equal amounts, 25% each. As the polymer becomes incrci(sitgly stereoregular, the rclaitive amounts of mm and rr change so that one increases to be greater than the other. S.I. is the ratio of the larger of mm or rr to the smaller of mm or rr and is always positive and greater than 1. S.I. expresses in a numerical way how the stereochemical arrangement of monomer sequences shifts away from 1.00 for a random, atactic polymer to larger values characteristic of more stereoregular polymers. For example, $^{13}$C NMR analysis of polypropylene made using the catalyst {flu-C$_2$H$_4$-ind}ZrCl$_2$ (activated with methylaluminoxane) showed that the mm:mr:rr ratio is 26:31:43, so the S.I. is 43/26, or 1.65.

The S.I. does not indicate whether a particular polymer is isotactic or syndiotactic but this can be shown by adding the letter S or I after the S.I. value. In the example above, one would have 1.65S, indicating that the polymer is syndiotactic-rich. However, this distinction matters little when S.I. values are large, because highly iso- or syndiotactic-rich polymers share properties outside of the scope of the present invention: high crystallinity, opacity, high melting points, stiffness and insolubility in aromatic and aliphatic hydrocarbons. These properties begin to occur in polypropylenes whose stereoregularity indices are greater than about 6.6.

The asymmetry parameter of a metallocene catalyst can be related to the stereoregularity index of the polypropylene that it produces and therefore to the physical and mechanical properties of the polymer. Polypropylenes produced with metallocene catalysts whose asymmetry parameters are about 1.0 arc essentially atactic with stereoregularity indices between about 1.0 and about 1.3.

The stereochemical irrelevance of large bulky groups that are placed in positions far removed (i.e., greater than 5 Å) from the reaction center is illustrated by the metallocene catalysts {(2,7-R₂flu)-C₂H₄-(flu)}ZrCl₂ (wherein R=t-butyl or p-tolyl). These produced polypropylenes with S.I. values of 1.26 and 1.08, respectively, and whose NMR spectra were consistent with that of an atactic polymer.

Asymmetry in the bridging element has little effect on the stereochemical outcome of the polymerization. For example, polypropylene obtained with the catalyst {flu-CH₂-SiMe₂-flu}ZrCl₂ is atactic and has an S.I. value of 1.04.

Figure 3:
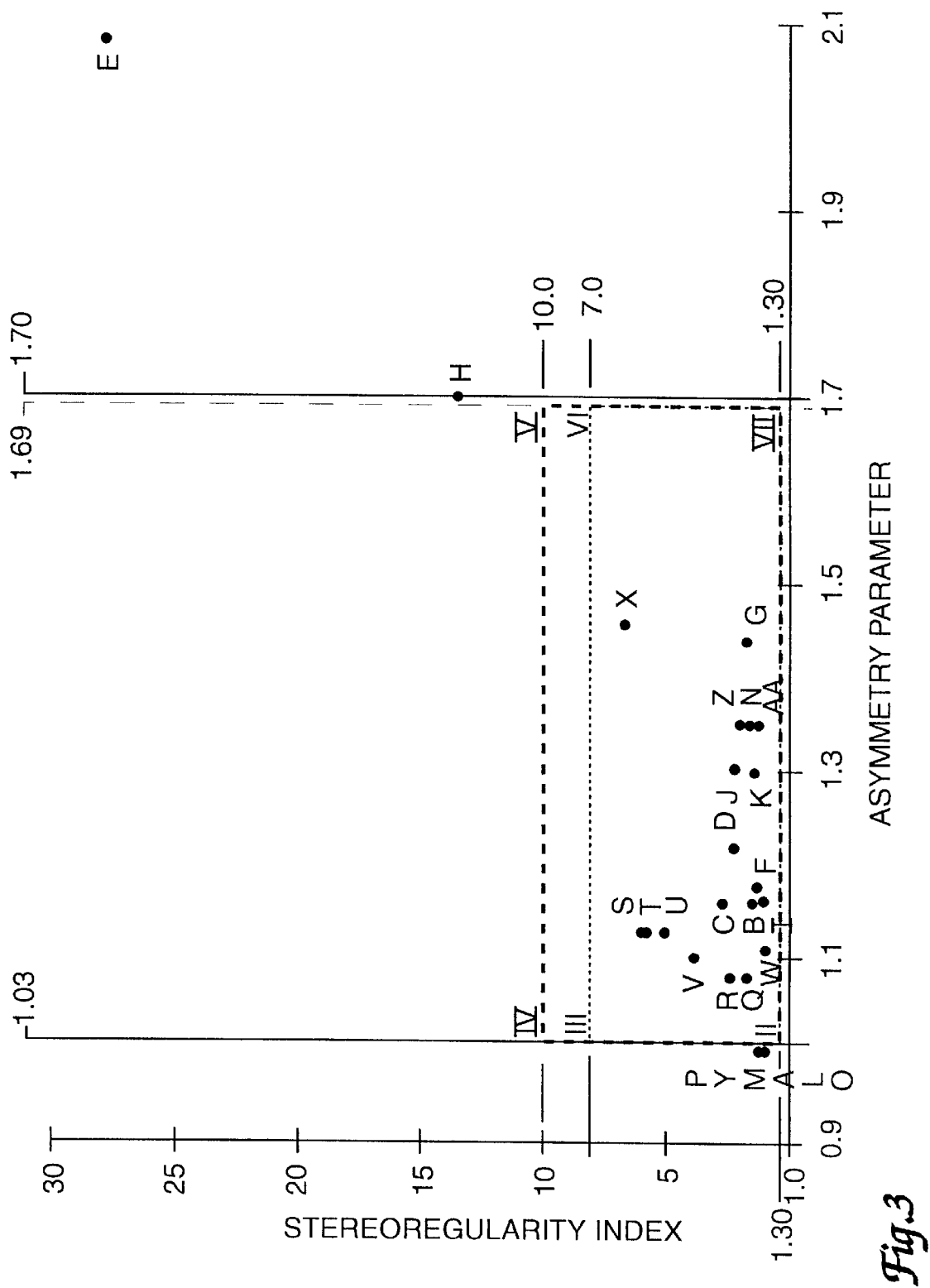
FIG. 3 shows the relationship between stereoregularity index (S.I.) and asymmetry parameter (A.P.) for metallocene catalyst-polypropylene pairs of the invention; preferred pairs fall within area II, IV, V, VII; more preferred pairs fall within area II, III, VI, VII.

When the asymmetry parameter of a metallocene catalyst is above about 1.69, both stereoregularity and crystallinity of the product polypropylene rise sharply. This is illustrated by FIG. 3 and Table 1. For example, the catalyst {4-(1-naphthyl)-2,7-di-t-butyl-flu-C₂H₄-flu}ZrCl₂ (18H, below, A.P.=1.70) produced crystalline, very isotactic-rich polypropylene with mm:mr:rr 80:14:6 (stereoregularity index= 13.3). The catalyst {flu-CMe₂-Cp}ZrCl₂ is even more asymmetric and has a very large A.P. value of 2.09 (18E, below). It is reported (Ewen, et al., in *Catalytic Olefin PolymerizLtion*, T. Keii and K. Soga, eds., Elsevier (1990), p. 439) to produce highly isotactic polypropylene with an S.I. value of 27.3.

Thus, the shape of a inetallocenc catalyst, reflected in its asymmetry parameter, is a critical determinant of polymer stereoregularity and crystallinity. Catalysts whose A.P. values lie between about 1.03 and 1.69 have been found to be useful in the preparation of hybrid poly)ropylenes, that is, polypropylenes having physical and mechanical properties that are not characteristic of the extremes represented by either atactic or very stereoregular materials, but rather are intermediate between the two limiting cases. Such catalysts enable synthetic access to a continuum of new polypropylenes, with a continuum of properties, that lies between these two extremes. Hybrid polymers can have a wide variety of microstructures and their S.I. values can vary from 1.30 to 10.00. In FIG. 3, area II, IV, V, VII indicates the range of asymmetry parameters and stereoregularity indices found to be associated with these new, hybrid polymers of the present invention.

While many of the catalysts of this invention contain fluorenyl moieties, their presence is not necessary in order to obtain polypropylenes in the range of S.I. values claimed. This is illustrated by Example 18-V, below, in which the 6-membered benzene rings have been catalytically hydrogenated; in this way, they become tetramethylene,.(CH₂)₄, moieties connected to cyclopentadienyl rings. This example underscores the fact that it is not the specific nature of the cyclopentadienyl-type rings in the catalysts that determines steroregularity. Rather, it is the shape of the catalyst (taken as a single molecular unit) expressed through its asymmetry parameter (A.P.) that controls the stereoregularity index.

Metallocene catalysts useful in the invention can be represented generally by {(ligand 1)-bridge-(ligand2}MX₂, wherein ligand1, ligand2, bridge, M, and X are as previously defined and wherein the metallocene catalyst exhibits an asymmetry parameter of 1.03 to 1.69. The metallocene catalysts provide propylene polymers as defined above.

Preferably, the catalysts exhibit one or more of i) a stereoregularity index between 1.30 and 10.00, ii) a heat of fusion (ΔH$_{fus}$) that is less than 50% of the ΔH$_{fus}$ of either isotactic or syndiotactic polypropylene, and iii) optical clarity.

Preferably, metallocene catalysts of the invention comprise the structure

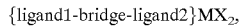

{ligand1-bridge-ligand2}MX₂, wherein ligand1 and ligand2 are different and are selected from the group consisting of fluorenyl, indenyl, 4,5-dihydrocyclopentaphenanthryl, and cyclopentaphenanthryl, optionally having substituents as described above, hridcge is selected from the group consisting of C₂H₄, SiPh₂ and Si(CH₃)₂, M is Zr, X is individually selected from the group previously defined, and the catalyst aisymmetry parameter is between 1.03 and 1.50.

Preferably, metallocene catalysts comprise various substituent groups oil tile ligand rings, typically alkyl or alkenyl groups, preferably C₁–C₂₀ alkyl, are placed near the metal-containing reactive center in the catalyst (i.e., within 5 Å).

Metallocene catalysts of the present invention having asymmetry parameters between about 1.03 and 1.50 can be subdivided into two classes, designated A and B, below, depending on whether or not they possess a mirror plane of symmetry bisecting the MX₂ angle. This mirror plane is represented by sigma v (σ$_v$) in FIG. 1.

Catalysts of Type A have such a symmetry plane. They produce novel polypropylenes whose molecular weight distributions, as assessed by gel permeation chromatography (GPC) of toluene solutions, typically are monomodal. These polymers are syndiotactic-rich, that is % rr>% mm, and they are optically clear and transparent. They may be noncrystalline or only slightly crystalline. That is, they may either exhibit no melt endotherm by differential scanning calorimetry (DSC) analysis or may exhibit an endotherm corresponding to less than 50% crystallinity, preferably less than 40% crystallinity.

The percentage of crystallinity of an isotactic-rich polypropylene approximately equals the ratio of the observed heat of fusion (ΔH$_{fus}$) to the literature heat of fusion of 100% crystalline isotactic polypropylene. The percent crystallinity of a syndiotactic-rich polypropylene is calculated similarity but using instead the literature value of ΔH$_{fus}$ for 100% crystalline syndiotactic polypropylene. Furthermore, polypropylenes of the invention can exhibit melting transitions at temperatures at least 50° C. below the melting temperature for any known purely crystalline form of polypropylene. All show a glass transition at about 0° C., consistent with a substantially noncrystalline character. In addition, the X-ray diffraction (XRD) patterns can show weak, sharp lines due to a very minor crystalline component superimposed upon a broad, structureless peak arising from the predominant, noncrystalline component.

Depending on the catalyst design and polymerization conditions (see below), the rr content of polypropylenes of the invention resulting from use of Type A catalysts can range from about 35% to greater than 65%. Stereoregularity indices can vary between 1.30 and 10.00 preferably in the range of 1.30 to 7.00, and most preferably 1.80 to 6.30. These polymers are soluble in toluene at room temperature. Films made by the latter technique are transparent, elastomeric and show no evidence of haze. It is now appreciated that the properties of the propylene polymers such as modulus, particularly modulus at 150° C., crystallinity, and tensile strength, are very sensitive to, and increase sharply with, small changes in rr content. This has not been taught in the prior art.

The weight average molecular weight of thie polymers of the invention can be in the range of 70,000 to 1,000,000 preferably 80,000 to 750,000.

When the weight average molecular weight of these polymers is between about 70,000 and 200,000, more preferably 80,000 to 200,000, and when the S.I. is in the range of 2.5 to 4.0, preferably about 3.0, the materials are both elastic and tacky. They may be used, e.g., to make pressure sensitive adhesives.

As molecular weight increases, an unexpected property, resistance to flow at elevated temperature, develops in these elastomers. As an illustrative example, a novel polypropylene having an S.I. of 2.6 was prepared using the metallocene catalyst {CPA-C$_2$H$_4$-flu}ZrCl$_2$(A.P.=1.08) (I) (referred to in Table 1, below, as 18Q).

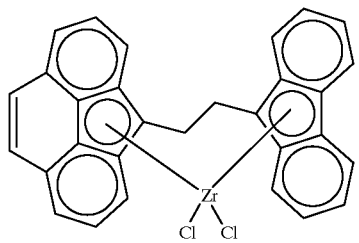

I

Figure 4:
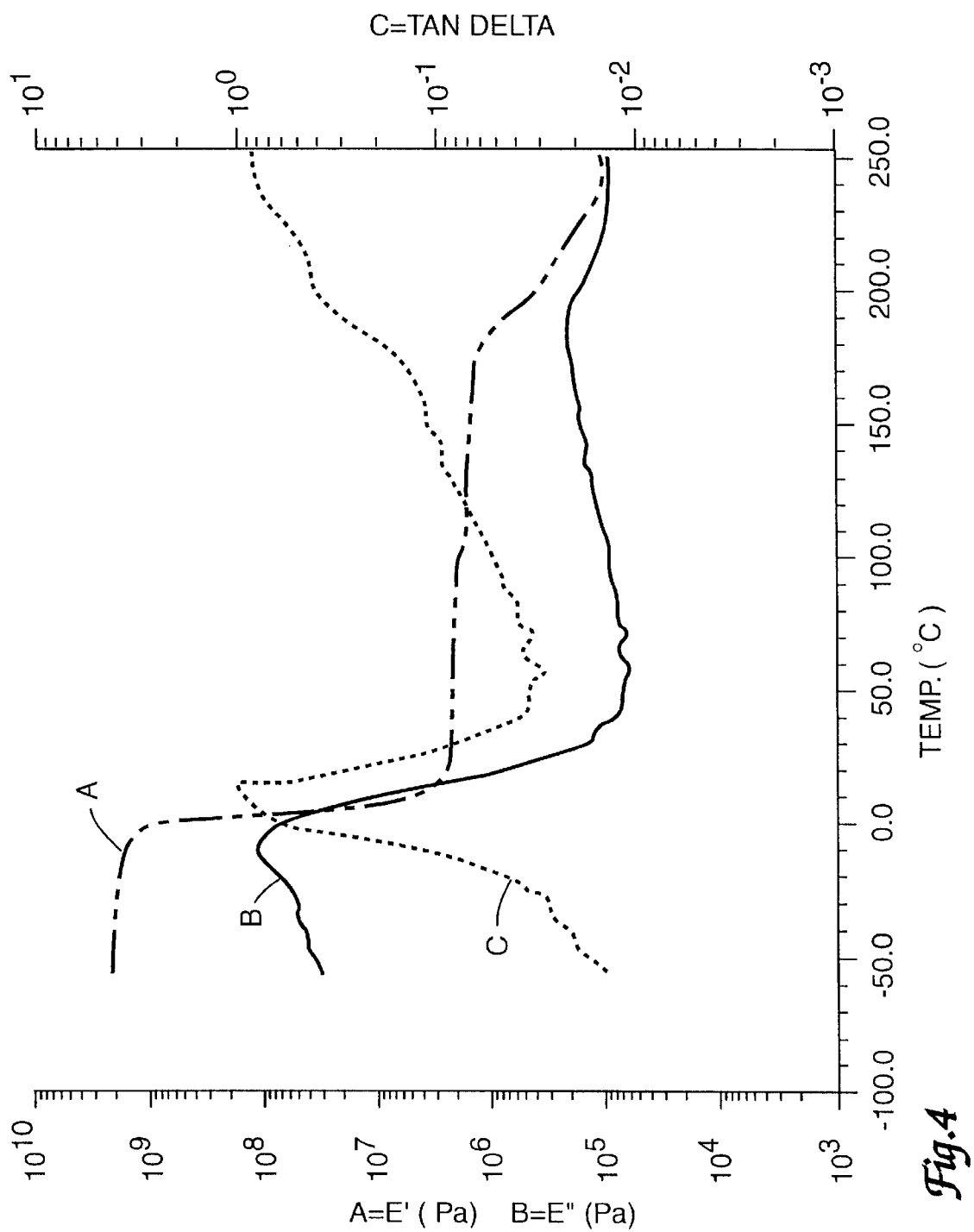
FIG. 4 shows the dynamic mechanical analysis spectrum and the variation of tensile storage modulus E', loss modulus E" and loss tangent (tan delta) with temperature for a polypropylene prepared using a metallocene catalyst in accordlice with the invention (see Example 19, below).

This compound has one ligand in which a vinylene or —CH═CH— "strap" joins the 4 and 5 positions of a fluorene ring group, which has the systematic name 4H-cyclopenta{d,e,f}phenanthrene, abbreviated as CPA. In FIG. 4, it can be seen that dynamic mechanical analysis of the resulting polypropylene shows that the polymer resists flow up to about 170° C. The curve relating storage modulus (E') and temperature exhibits a broad, rubbery plateau between about 25° C. and 170° C. One interpretation of the DMA spectrum can be that the material behaves as though it were crosslinked or contained a hard structural, load bearing phase in a softer continuous matrix. However, the polymer is completely soluble in toluene at room temperature, which is inconsistent with crosslinkinig, and it exhibits neither a mielt endotherm nor sharp X-ray diffraction lines, which indicates the absence of crystallinity. In contrast, both atactic polypropylene and commercial syndiotactic polypropylene begin to flow at about 100° C. The shear modulus is 6.0×10$^5$ Pa between 25 and 150° C. and is much higher than that of atactic polypropylene, 3.0×10$^5$ Pa at 150° C. The polymer is highly elastic and exhibits only a 4.5% inelastic deformation after 10% of strain (ASTM DI1774-90).

As polymer stereoregularity increases, room temperature shear storage modulus (E') increases significantly. For example, a novel polypropylene prepared using the novel metallocene catalyst {H$_2$CPA-SiMe$_2$-flu}ZrCl$_2$ (II) (the abbreviation H$_2$CPA indicates hydrogenation of the vinylene "strap" of CPA), having an A.P. of 1.13 (18T, below), yields polypropylene having an rr content of 59% and an S.I. of 5.9.

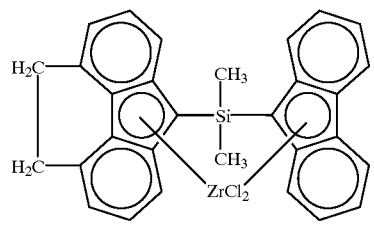

II

Figure 5:
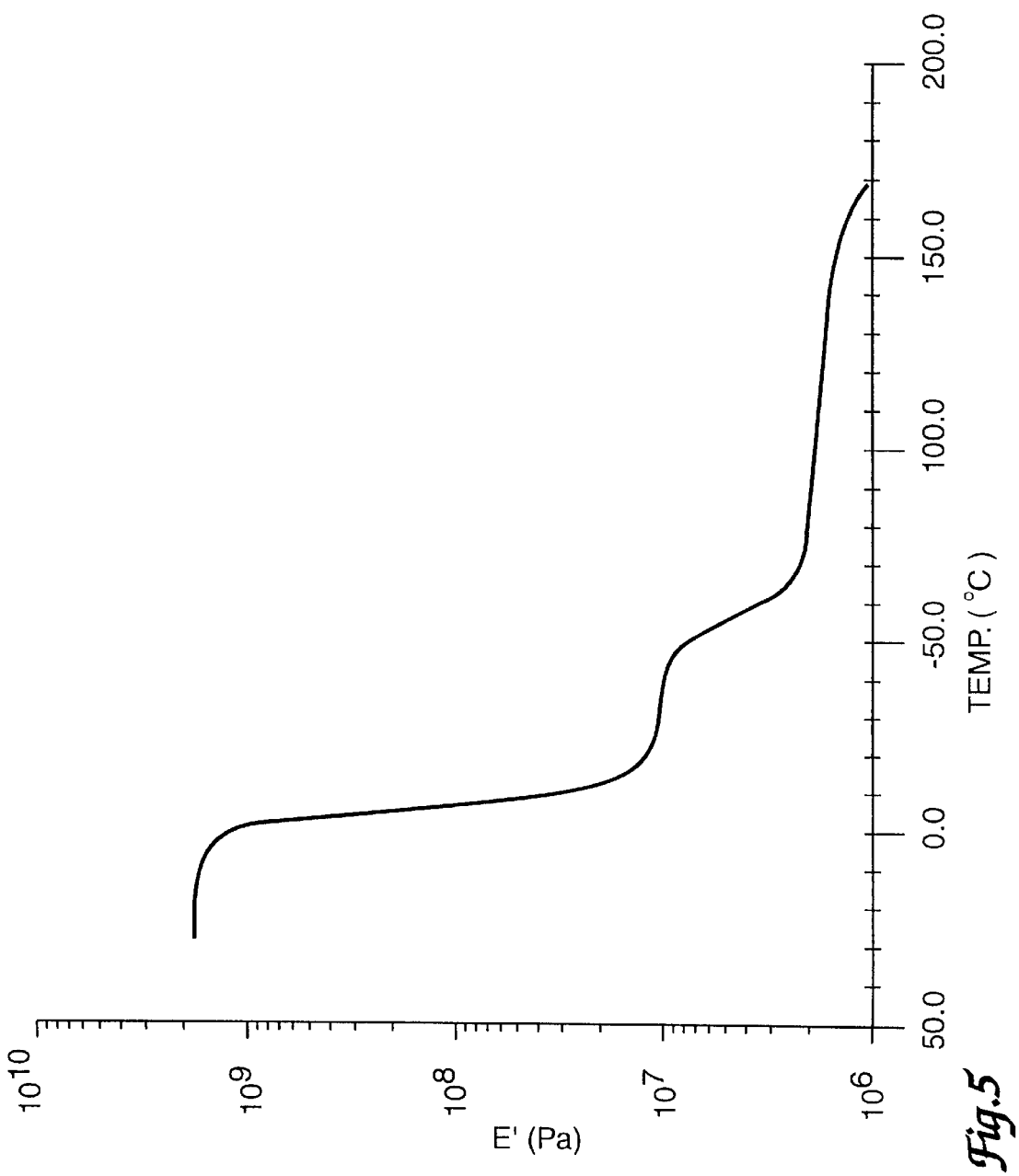
FIG. 5 shows the variation of tensile modulus E' with temperature, after 28 days of aging at 23° C., for a polypropylene prepared using a metallocene catalyst in accordance with the invention (see Example 20, below).

The subtle changes in catalyst design lead to a polymer that is considerably stiffer at room temperature, with a E' value for pressed films of 13.0×10$^6$ Pa. It exhibits a melt endotherm at 48° C.; the heat of fusion, 12 J/g, corresponds to a crystallinity content of 12/50 or 24 weight % (50 J/g is the literature heat of fusion ($\Delta H_{fus}$) oftotally syndiotactic polypropylene). The crystallinity is due to small amounts of an oriented syndiotactic polypropylene phase. Significantly, both DSC and X-ray diffraction show that the crystalline phase has disappeared at a temperature of about 60° C., yet a plot of E' versus temperature (FIG. 5) again demonstrates a broad, rubbery plateau, with a value of 2.20×10$^6$ Pa, from about 50° to about 170° C., at which temperature the material begins to flow. Between 50° and 170° C., the plot of E' versus temperature strongly resembles that of FIG. 4, trace A, 18Q, in Table 2, below, where the polypropylene had an S.I. of 2.8. Therefore, resistance to flow at elevated temperatures displayed by these two polymers cannot be attributed to crystallinity, the presence of which has heretofore been assessed, as it is here, by DSC and X-ray diffraction. Without wishing to be bound by theory, it is proposed that this phenomena, which to our knowledge has never before been reported for non-crystalline polypropylene, may be due to nanocrystallinity, that is, crystalline or structurally-ordered domains that are very much smaller, perhaps 150 Å, than has previously been considered as important. Small angle light scattering experiments disclose that additional orientation of large crystallites (i.e., those melting at about 48° C.) in this polymer may be achieved by stretching and which diffract X-rays.

This polymer is exceptionally elastic and exhibits essentially no inelastic deformation following extension to 10% strain. The presence of a low-melting component confers heat sealability upon the polymer. Films of the material may be fused together above about 50° C.

Figure 6:
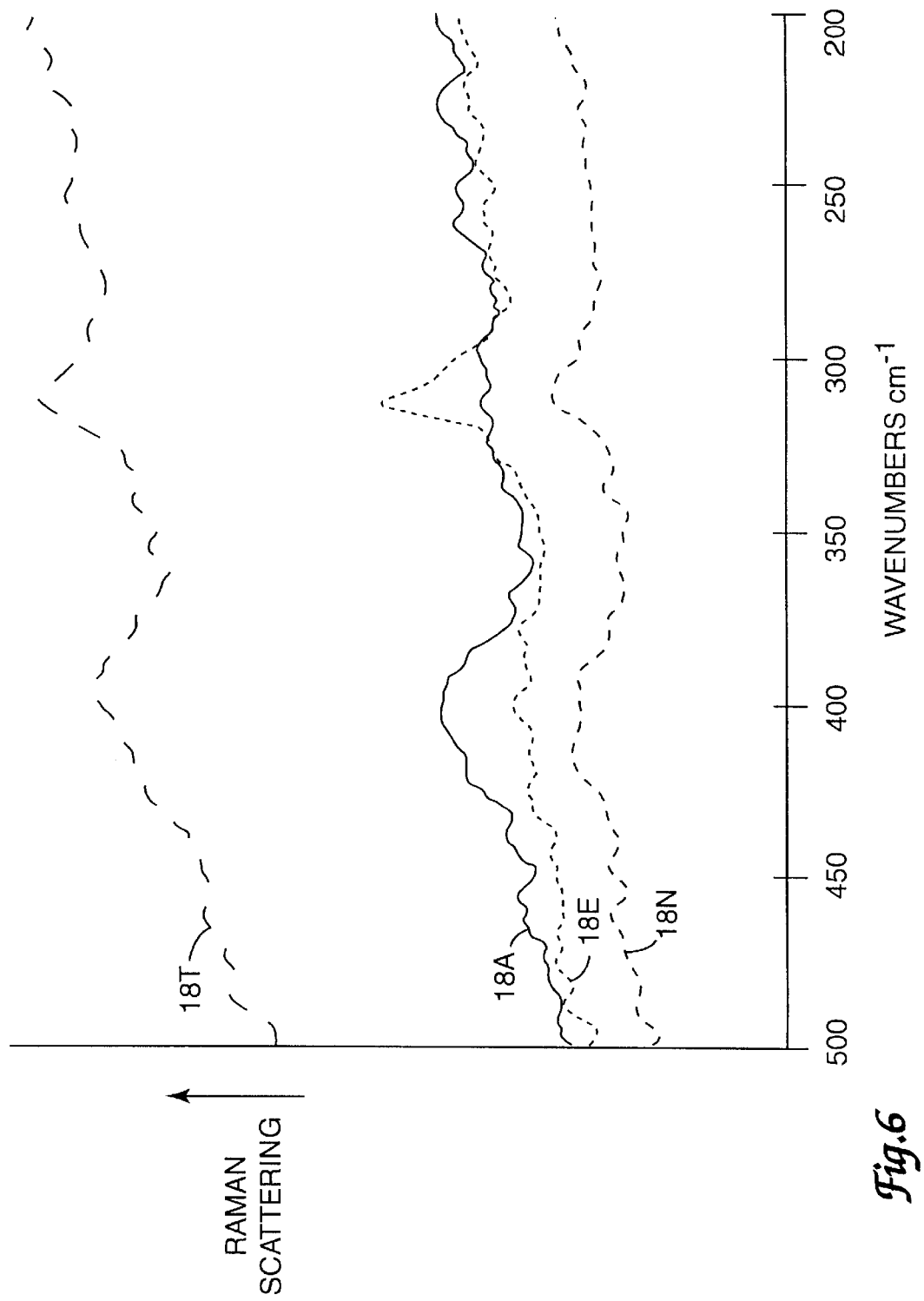
FIG. 6 shows Raman scattering traces of polypropylenes of the invention (18T and 18N) and comparative polypropylenes (18A and 18E).

Raman spectra can be used to characterize the hybrid nature of propylene polymers. Spectra in the 200–500 cm$^{-1}$ skeletal stretching region are shown in FIG. 6. Atactic polypropylene (Example 18A below) has a broad scattering peak at about 400 cm$^{-1}$ and crystalline syndiotactic polypropylene (Example 18E) has a sharp peak at 313 cm$^{-1}$. The spectra of polymers from (Examples 18 N and 18 T, below) show bands at both about 400 and 310 cm$^{-1}$ due both heterotactic and homotactic sequences, respectively, in the same chain. That is, a single chain, if it were extracted from the polymer mass, would be seen to contain both types of sequences.

Table 7, below, summarizes some of the physical properties of polypropylenes obtained with the novel catalysts of the invention.

A noteworthy result is that crystallinity (as detected by DSC and XRD) is present generally when the S.I. index is about 3.9 or greater.

Table 2, below, presents data that show how S.I. (and % rr content) change with catalyst design and with polymerization conditions. It reveals how changes in catalyst structure and polymerization temperature may be used to change the polymer stereoregularity index and polymer physical properties.

Several trends can be found:

(1) Connecting the 4 and 5 positions of a fluorene ligand (i.e., dihydrocylopentaphenanthrenes of Examples 18S, 18T, and 18U, below) via a —$CH_2$—$CH_2$— unit provides a catalyst that is more stereoregulating (higher S.I. and % rr content) than one having a —CH=CH— unit in the same position (i.e., cyclopentaphenanthrenes of Examples 18Q and 18R). Both groups are more effective in controlling stereoregularity than is a single methyl group at the 4 position (18W) or even two methyl groups at the 4 and 5 positions as found, for example, in compounds having the general formula shown in Table 2 but in which the 4,5-dimethylfluorenyl group replaces (strap)flu;

(2) Stereoregularity and polymer molecular weight both decrease with increasing polymerization temperature (Examples $18Q_1$ vs. $18Q_2$; $18T_1$ vs. $18T_1$; $18S_1$ vs $18S_2$); the temperature effect on $M_w$ is much larger than on S.I.;

(3) Otherwise identical metallocenes with a $SiMe_2$ bridge connecting the two ligands (Examples 18R, 18T, and 18U) wherein Me=methyl are more stereoregulating than those having a —$CH_2$—$CH_2$— bridge (18Q and 18S);

Small changes in stereoregularity index (and % rr content) bring with them substantial changes in polymer properties, as explained above. Thus, catalysts of the invention make possible synthesis of a wide variety of new polypropylenes whose % rr content varies from 29 to 73%, preferably 29 to 65%, a range of 36% when considering both Type A and Type B catalysts. This is in advantageous contrast with prior art catalysts, which enabled a range of only 8% (from 74-82%) in rr content (U.S. Pat. No. 5,459,218).

The pentad intensities of polypropylenes produced by Type A metallocenes of the invention can be described in terms of a single catalytic site. They follow Bemoullian statistics based upon a single, unique value of $P_r$, the probability of obtaining a syndiotactic insertion each time a propylene monomer is added to the growing polymer chain. $P_r$ values can be used in a Monte Carlo calculation to determine the length distributions of all-r sequences and their weight percent abundances.

Metallocenes of type B have the general structure {$R^1$-ligand1-bridge-ligand2}$ZrCl_2$, wherein ligand1, ligand2, bridge, and $R^1$ have been previously defined. The mirror plane of symmetry bisecting the Cl—Zr—Cl angle is absent in Type B metallocenes; in fact, these metallocenes have $C_1$ point group symmetry. The microstructure of polymers obtained using Type B metallocenes of the invention, as deduced from $^{13}C$ NMR analysis, cannot be described in terms of a single catalytically active site.

Polypropylenes obtained using Type B catalysts of the invention can be either syndiotactic- or isotactic-rich. They are elastomeric but lack the resistance to flow at elevated temperatures found in high molecular weight polymers obtained using Type A catalysts. Table 3 summarizes results obtained using Type B catalysts. It can be seen that the polymer microstructure, i.e. whether syndiotactic- or isotactic rich, appears to vary unpredictably depending on the nature of the substituent on the indenyl ring and, more surprisingly, on the nature of the bridging moiety connecting the indenyl and fluorenyl moieties of the ligand. Unlike the polypropylene elastomers prepared by Collins et al. (supra), which had a nimmm content of 38% or greater, the maximum mmmm content in elastomeric polymers prepared using catalysts of the invention is 31%, and the mm triad content was in range of 24 to 50 percent. This indicates that materials have been obtained that are distinguishable and very different.

Polymers listed in Table 3, below, also exhibit large polydispersity (PD) values (i.e., greater than 2.5), that is, the weight average molecular weight $M_w$ divided by the number average molecular weight $M_n$. In fact, GPC analysis discloses that the molecular weight distributions of polymers obtained using Type B catalysts are actually bimodal and in the case of catalysts 18B and 18I, possibly triniodal. In Table 3, the values given in parentheses represent the percent composition of each major constituent. That is, these catalysts appear to produce two different kinds of polypropylene. The two kinds are differentiable by their distribution of moleculair weights and peak molecular weights, $M_p$. Neither of the two kinds of polymers corresponds to a highly stereoregular, e.g., crystalline, component because all of the polymers are soluble in or completely extractable by hydrocarbons such as toluene or heptane. In other words, the two kinds of polypropylene produced by a given catalyst of the invention cannot be fractionated according to solubility. Lack of significant levels of crystallinity is affirmed by the transparency of pressed films of the novel polymers.

A particularly interesting elastomer is produced using the class B metallocene {ind-$C_2H_4$-flu}$ZrCl_2$ (Examples 3, 4 and 18N). It has a tensile strength at break and modulus (at small strain) of 718 and 2300 KPa, respectively. lThe material is exceptionally elastic or stretchy: elongations without break of 4,000% or more were achieved and a maximum elongation of 5200% has been achieved and the sample did not break. U.S. Pat. No. 5,595,080 describes a different homopolymer of propylene obtained by a catalyst of a different class having an ultimate elongation of 3000% that was reported as the highest known value for elongation.

This invention also encompasses heteropolymers, that is, co-polymers of propylene with up to 25 mole per cent of 1-olefins containing up to 18 carbon atoms, such as 1-hexene, 1-octene or 1-octadecene, which serve to render the polymers softer and more flexible, lower the glass transition temperature, or to facilitate their flow and extrusion at elevated temperatures. One or more tackifiers known in the art may be added to the polymers in order to lower their glass transition temperatures. Two or more polymers of this invention may be mixed together to provide blends having intermediate properties. A similar result can be achieved by polymerizing propylene, along with optional comonomers as described above, in the presence of two or more catalysts of this invention. Additionally, various antioxidants, such as Irganox 1010™, may be added to enhance thermal stability of the polymers.

Metallocenes of the type {ligand1-bridge-ligand2}$MX_2$ require treatment with an activating cocatalyst in order to produce an active catalyst. When X is $CH_3$, $CH_2C_6H_5$ or other alkyl or aralkyl groups, $(C_6H_5)_3C(+)$ salts of various noncoordinating anions can be used. Also useful are onium salts of the type $R^5R^6R^7QH(+)$, wherein Q=N or P, and $R^5$, $R^6$, and $R^7$ can be the same or different and are selected from the group consisting of $C_1$–$C_{20}$ straight-chain group or branched alkyl group, $C_6$–$C_{20}$ aryl, and $C_3$–$C_8$ cycloalkyl groups. Illustrative are (n-C$_4$H$_9$)$_3$NH(+), PhN(CH$_3$)$_2$H(+) and Ph$_3$PH(+). Effective noncoordinating anions include, but are not limited to, (C$_6$F$_5$)$_4$B(−), (C$_6$F$_5$)$_3$BCH$_3$(−) and B$_{11}$CH$_{12}$(−).

When X=halogen, the preferred activator compound is an aluminoxanle. Aluminoxanes are prepared by the partial, controlled hydrolysis of trialkylaluminums, See, for example, U.S. Pat. No. 4,752,597, col. 10, line 6 ff, which is incorporated herein by reference. Particularly preferred is methylaluminoxane, (CH$_3$ AlO)$_x$ which is obtained by controlled hydrolysis of trimethylaluminum. Unreacted trimethylaluminum may be removed from commercially available methylaluminoxane by vacuum distillation or other methods known in the art, but such removal may not be necessary in order to obtain highly active catalysts. Indeed, trialkylaluminum compounds may be optionally added to the catalyst solution or monomer to scavenge harmful impurities such as adventitious oxygen or water. Methylaluminoxane can be used in excess so that the Al:M (wherein M=Zr or Hf) ratio is 2:1 to 2000:1 with the preferred range being 10:1 to 1000:1.

The active catalyst is prepared by combining the metallocene and the activator component in a nonreactive solvent such as toluene or xylenes and, optionally, nonreactive hydrocarbons such as heptane or cyclohexane. The active catalyst may be used directly or it may be impregnated onto a solid carrier such as silica. It is also possible to combine two or more metallocenes and to then treat this mixture with an activator component and to produce in this way a catalyst blend that, when contacted with propylene, will produce a polymer blend.

It has been found that polymer properties such as stereoregularity and molecular weight are greatly affected by the propylene concentration in the polymerizing reaction mixture and also by how it changes during the course of the reaction. Thus, although catalysts of this invention may be used under a wide variety of conditions, they are preferably used to prepare polypropylene in the absence of solvent. Propylene then serves as both monomer and diluent; its initial concentration, about 12M, changes little until high conversions to polymer have occurred. This was the case in Examples 4 and 18N, below.

Polymerization may be carried out as a batchwise slurry, solution or bulk reaction, or as a continuous process. In continuous polymerization, propylene, comonomer (if any) (as described above), and catalyst are continually supplied to a reactor in amounts equal to those removed from the reaction zone in the product stream. When the catalyst is supported on a solid carrier, gas phase polymerization in a fluidized bed can be conducted.

Processes for preparation of polypropylene in which no solvent is added, i.e., in which propylene serves as both monomer and diluent, are preferred. When solvents are used, preferably they are hydrocarbons, more preferably toluene or cyclohexane. Polymerization to produce new polypropylenes of this invention may be carried out at a pressure of 69 to 6890 Kpa (about 10–1000 psi). A wide range of reaction temperatures is possible but the range −20° to about 120° C. is preferred. Optionally, hydrogen gas may be added to modify the product molecular weight. For example, as is known in the olefin-polymerization art, controlled addition of hydrogen gas to a catalytic olefin polymerization reaction can lower the molecular weight of the polymer thus obtained, relative to the same polymerization procedure carried out in the absence of hydrogen. See, for example, U.S. Pat. No. 3,051,690, entire document, particularly Examples 1–32.

After processing at elevated temperatures, e.g., pressing films at about 170° C., mechanical strength develops at rates dependent on thermal treatment. The process may be hastened by brief cooling, e.g., in ice water, or by passing the polymers over a chill roll or by the addition of a small amount of crystallization aid such as Millad™ 3905 (Milliken Chemical Co., Spartanburg, N.C.).

Unsymmetrical metallocenes, i.e., those having an A.P. greater than 1.03, can be prepared using dissimilar ligands, e.g., ligand1 and ligand2. Such metallocenes containing an —SiMe$_2$— bridge may be prepared from the reaction of a compound such as {ligand1}SiMe$_2$Cl (prepared as described in U.S. Pat. No. 5,026,798, Example C, Part 2) with the conjugate base of ligand2.

The present invention also describes a novel process for the synthesis of compounds of the type H{ligand1-C$_2$H$_4$-ligand2}H. For example, 2-(9-fluorenyl)ethanol, abbreviated as H{flu-CH$_2$—CH$_2$—OH}, in a hydrocarbon solvent such as toluene, heptane or cyclohexane or mixtures of such solvents, is treated with exactly one equivalent of a base having sufficient basicity to deprotonate the hydroxyl group. n-Butyllithium is preferred. Next, reaction with a highly fluorinated alkyl sulfonyl fluoride wherein alkyl has 1 to 20 carbon atoms, preferably a perfluoroalkyl sulfonyl fluoride R$_f$SO$_2$F wherein R$_f$ is an alkyl group having 1 to 20 carbon atoms, e.g., trifluoromethanesulfonyl fluoride, yields H{flu-CH$_2$—CH$_2$—OSO$_2$R$_f$}. In a second step, the conjugate base of ligand2 is used to displace R$_f$SO$_3^-$. Thus, for example, reaction of flu-C$_2$H$_4$-OSO$_2$CF$_3$ with the lithium salt of cyclopentaphenathrene produces 1-(9-fluorenyl)-2-(cyclopentaphenanthrenyl)ethane which can be abbreviated as H{CPA-C$_2$H$_4$-flu}H.

In the above reaction sequence, R$_f$ is independently selected from the group consisting of highly fluorinated or perfluorinated alkyl radicals.

The R$_f$ alkyl group may contain from 1–20 carbon atoms, with 1–20 carbon atoms preferred. The R$_f$ groups chains may be straight, branched, or cyclic and preferably are straight. Heteroatoms or radicals such as divalent oxygen, trivalent nitrogen or hexavalent sulfur may interrupt the skeletal chain, as is well recognized in the art. When R$_f$ is or contains a cyclic structure, such structure preferably has 5 or 6 ring members, 1 or 2 of which can be heteroatoms. The radical R. is also free of ethylenic or other carbon-carbon unsaturation: e.g., it is a saturated aliphatic, cycloaliphatic or heterocyclic radical. By "highly fluorinated" is meant that the degree of fluorination on the chain is sufficient to provide the chain with properties similar to those of a perfluorinated chain, i.e., at least 75 percent fluorination. More particularly, a highly fluorinated alkyl group will have more than half the total number of hydrogen atoms on the chain replaced with fluorine atoms. Although hydrogen atoms may remain on the chain, it is preferred that all hydrogen atoms be replaced with fluorine to form a perfluoroalkyl group, and that any hydrogen atoms beyond the at least half replaced with fluorine that are not replaced with fluorine be replaced with bromine and or chlorine. It is more preferred that at least two out of three hydrogens on the alkyl group be replaced with fluorine, still more preferred that at least three of four hydrogen atoms be replaced with fluorine and most preferred that all hydrogen atoms be replaced with fluorine to form a perfluorinated alkyl group.

Surprisingly, the trifluoromethane sulfonate prepared by the method of the present invention is stable for at least 2 days at room temperature (about 23° C.), in contrast to the previously-reported method (Rieger et al., *Organometallics* 13, 647 (1994)), wherein the same compound was obtained in a form that decomposed rapidly above 0° C.

Other perfluoroalkylsulfonyl fluorides, such as $C_4F_9SO_2F$, which is a liquid at room temperature, can be used in place of low boiling $CF_3SO_2F$.

Compounds of the type H{ligand1-bridge-ligand2}H can be converted into to their titanium, zirconium or hafnium dihalide complexes by methods long known in the art. As an illustrative example, reaction of H{CPA-$C_2H_4$-flu}H with two equivalents of butyllithium yields the salt $Li_2$(CPA-$C_2H_4$-flu) which, when allowed to react with $ZrCl_4$ or $ZrCl_4$.2(tetrahydrofuran) or $ZrCl_4$.$CH_3OC_2H_4OCH_3$, affords {CPA-$C_2H_4$-flu}$ZrCl_2$. The metallocene is obtained as a finely divided powder. It may be freed from lithium chloride and other byproducts and impurities by extraction with a nonreactive solvent such as dichloromethane. However, this purification step typically is not necessary and the crude metallocene can be used as such to prepare a catalyst. Other metal alkyls, such as butylsodium or dibutylmagnesium, or benzylpotassium, or metal hydrides such as potassium hydride may be used in place of butyllithium.

Polypropylenes of this invention provide thermoplastic elastomers which can be used as adhesives, binders, and films. These polymers may be used alone or admixed with fillers or adjuvants, such as carbon black, glass fibers, metal particles or whiskers, or cellulose. They may be used in combination with colorants and pigments such as iron oxide. They may be inicorporated into blends with other polymers, such polyhexene or polyoctene, or with crystalline or amorphous polypropylenes, or as multilayer, laminated construction with these same polymers. Amounts of adjuvants or fillers added can vary depending on the application desired.

Objects and advantages of this invention are further illustrated by the following examples, but the particular materials and amounts thereof recited in these examples, as well as other conditions and details, should not be construed to unduly limit this invention.

EXAMPLES

Methylaluminoxane was obtained from Albemarle Corp., Baton Rouge, La., as a 30% solution in toluene. This was diluted 1:2 (v/v) with dry, oxygen-free toluene (vacuum distilled from triisobutyl aluminum) to produce a solution having an aluminum concentration of 1.7M.

Unless otherwise indicated, reactions were carried out in an atmosphere of dry, oxygen free nitrogen. Solvents, when used, were dried with molecular sieves or purified by distillation from sodium-benzophenone. Uncomplexed, organic ligands were handled and purified in air but metallocenes, which usually exhibited some degree of sensitivity to atmospheric moisture, were purified and stored in a nitrogen-filled drybox.

Unless otherwise indicated, all chemicals were obtained from Aldrich Chemical Co., Milwaukee, Wis. The compounds 1-methyl- and 1-trimethylsilylindene were prepared according to the method of Ready et al., *J. Organomet. Chem.*, 21, 519 (1996), and 1-phenylindene was prepared according to the method of Greifenstein et al., *J. Org. Chem.*, 46, 5131 (1981).

Polymerization Grade propylene (Matheson Gas Products, Seacaucus, N.J.) was passed through two Matheson model 6406A purifiers, connected in series, before use.

$^{13}$C NMR analyses to determine microstructure of polymers at the pentad level were obtained at 100° C. using 1,2-dichlorobenze,e solutions of the polymers with a Varian XL-500 spectrometer (Varian Associates, Inc., Palo Alto, Calif.) according to the method of Tonelli, "NMR Spectroscopy and Polymer Microstructure: The Conformational Connection", VCH, Deerfield Beach, Fla. (1989).

NMR chemical shifts are expressed in ppm relative to external $Me_4Si$ ($^1H$ and $^{13}C$) or $CFCl_3$ ($^{19}F$), positive shifts being downfield of the reference.

Positive ion mass spectra were obtained in electron impact mode using 70 eV electron beam energy. A lFinnigan FT/MS dual-cell Fourier transform mass spectrometer (Finnigan, San Jose, Calif.) with a 3.0 Tesla magnet was utilized to obtain the high resolution exact mass measurements. The samples were introduced into the mass spectrometer by using a direct insertion probe that was heated to 350° C. The electron impact (EI) mass spectral data was obtained using standard EI conditions. All mass spectra were acquired with a minimum resolving power of 3,000.

Number average molecular weights, $M_n$, weight average molecular weights, $M_w$, and peak molecular weights, $M_p$, for polymers were determined by gel phase permeation chromatography (GPC) on filtered solutions using a Waters 150C system (Waters Corp., Milford, Mass.) equipped with Jordi Associates Inc. (Bellingham, Mass.) 500A and mixed bed columns which were calibrated with polystyrene standards. Toluene at room temperature was used as solvent unless otherwise noted.

Wide angle X-ray scattering (WAXS) data was collected in a reflection geometry using a Philips vertical diffractometer (Philips Electronic Instruments Co., Mahwah, N.J.) equipped with variable entrance slits, graphite diffracted beam monochromator, and proportional registry of the scattered radiation. The radiation employed was copper K alpha with generator settings of 45 kV and 35 mA. Step scans were conducted between 5 and 55 degrees (2Theta) using a 0.04 degree step size and 4 second count time. For elevated temperature scans, a similar diffractometer fitted with a platinum strip furnace and Paar HTK temperature controller (Paar, Anton, USA, Ashland, Va.) was used. Software used to analyze the diffraction data was Philips PC-APD.

DSC data were obtained using a TA Instruments Model 2920 modulated differential scanning calorimeter (TA Instruments, Inc., New Castle, Del.). A linear heating rate of 5° C./min was applied with a perturbation amplitude of +1° C. every 60 sec. Samples were subjected to a cyclic heat-cool-heat profile ranging from –120° to 200° C. in a nitrogen atmosphere. Fleats of fision ($\Delta H_{fus}$) were determined by integrating heat flow curves.

Molecular modeling programs employed CAChe™ Satellite, ProjectLeader and molecular mechanics programs (all version 3.8) (Oxford Molecular Ltd., Oxford, United Kingdom) which were run on a Macintosh computer.

Counterions for the catalyst can be varied as is known in the art. Metallocene catalysts can also include Ti metal centers as is known in the art.

Example 1

2-(9-fluorenyl)ethyl trifluoromethane sulfonate

A 2.5M solution of n-butyllithium in hexane was added with stirring to 5 g 2-(9-fluorenyl)ethanol, flu-$CH_2$—$CH_2$—OH (prepared by the method disclosed in *Organometallics* 13, 647 (1994)), in 90 mL toluene. Addition was terminated when the reaction mixture became light orange; about 10 mL was required. The resulting solution of Li{flu-$CH_2$—$CH_2$—O} was cooled in a dry icc-acetone bath and 3.8 g trifluoromethanesulfonyl fluoride, $CF_3SO_2F$ (prepared according to U.S. Pat. No. 2,732,398, Example 1), was added by vacuum transfer. Alter warming to room temperature, any unreacted $CF_3SO_4F$ was removed by pumping. The desired compound was obtained as a colorless oil, 7.7 g (95%) by filtration of the reaction mixture followed by evaporation of solvents. Spectroscopic and chemical analysis confirmed the identity of the desired compound.

Example 2

{flu-$C_2H_4$-ind}

1-(9-fluorenyl)-2-(1-indenyl)ethane

To a solution of 21.0 g 2-(9-fluorenyl)ethanol, in 495 mL toluene was added dropwise with stirring 40 mL of a 2.5M solution of n-butyllithium in hexane. The resulting solution of Li{flu-$CH_2$—$CH_2$—O} was cooled to below –25° C. Then, 16.7 g $CF_3SO_2F$ was condensed into the reaction mixture. Tile temperature was allowed to rise to 25° C. and the reaction mixture was stirred for 6 h. Unreacted $CF_3SO_2F$ was removed by pumping about 10 mL of liquid into a dry ice-cooled trap. To the solution of flu-$CH_2$—$CH_2$—$OSO_2CF_3$ thus obtained was added a solution of 0.1 mole indenyllithium in 100 mL diethyl ether. After stirring for 12 h, solvents were removed under vacuum and the residue recrystallized in air from boiling heptane. The yield of white microcrystalline solid, mp 79–80° C., was 8.9 g (29%). Spectroscopic and chemical analysis confirmed the identity of the desired compound.

Example 3

{flu-$C_2H_4$-ind}$ZrCl_2$(designated 18N in Table 1, below)

A solution of 1.54 g 1-(9-fluorenyl)-2-(1-indenyl)ethane (Example 2) in 70 mL diethyl ether was treated with 4 mL 2.5M n-butyllithium in hexane. The resulting orange solution was stirred overnight, after which solvents were pumped away on a vacuum line. Zirconium chloride (1.17 g) and 75 mL hexane were added. The reaction mixture was vigorously stirred for 18 h then filtered. The solids were extracted with 350 mL dichloromethane. The filtered extract was evaporated and the residue slurried with 10 mL portions of 1:1 (v/v) dichloromethane-hexane to produce 0.61 g (26%) bright orange, powdery product that was collected on a filter and vacuum dried. Spectroscopic and chemical analysis confirmed the identity of the desired compound.

Example 4

Propylene Polymerization using {flu-$C_2H_4$-ind}$ZrCl_2$

A 0.017 g quantity of {flu-$C_2H_4$-ind}$ZrCl_2$ (Example 3) was dissolved in 16 mL methylaluminoxane solution. After 1 h, the solution was diluted with 10 ml, toluene and transferred to a 100 mL stainless steel cylinder fitted with a valve. 'Ihe cylinder was pressurized to about 5520 KPa (800 psi) with nitrogen gas, inverted and attached to a reactor containing 1816 g propylene at a temperature of 8° C. This reactor had a volume of about 8 L and was equipped with a thermocouple, an agitator and a jacket through which coolant could be circulated as needed in order to control the polymerization temperature. It was evacuated with a vacuum pump then backfilled with nitrogen prior to charging with propylene. Upon opening the cylinder valve, the catalyst solution was injected into the reactor. Over a 1 h period, the temperature rose to 28° C. and was maintained at that temperature for 4 more hours. Then, the reaction was terminated by venting unreacted propylene. The yield of polymer was 533 g. $^{13}C$ NMR analysis: 8.7% mmmm, 9.4% mmmr, 7.6% rmmr, 17.3% mmrr, 10.3% rmrr/mmrm, 3.8% nnrm, 22.0% rrrr, 14.1% mrrr, 6.9% mrrm, 25.7% mr, 31.4% mr and 43.0% rr. Spectroscopic and chemical analysis confirmed the identity of the desired product.

Example 5

{flu-$C_2H_4$-ind }$HfCl_2$

A solution of 1.54 g flu-$C_2H_4$-ind (Example 2) in 70 mL diethyl ether was treated dropwise with 4 mL 2.5 M n-butyllithiurm in hexane. The reaction mixture was stirred overnight, after which solvents were removed under vacuum. A slurry of 1.6 g $HfCl_4$ in 75 mL hexane was added and the reaction mixture was stirred for an additional 72 hours at 23° C., then filtered. Retained solids were extracted with 300 mL dichloromethane, and the extracts were evaporated to give a crude solid that was washed with five 20 mL portions of hexane, 20 mL 2:1 hexane:dichloromethane, then 20 mL hexane. After vacuum drying, the orange powdery solid product, {flu-$C_2H_4$-ind}$HfCl_2$, weighed 1.32 g (47%).

Spectroscopic and chemical analysis confirmed the identity of the desired compound.

Example 6

CPA-$SiMe_2$-flu

A solution of lithium cyclopentaphenanthrene (Li(CPA)) was prepared by adding 6.0 mL 2.5M n-butyllithiuin in hlexaine to 2.85 g cyclopentaphenanthrene dissolved in 50 mL tetrahydrofuran. The reaction mixture was stirred for 12 hr then treated with a solution of 3.87 g (9-fluorenyl) dimethylchlorosilane, flu-$SiMe_2Cl$ (prepared according to the method of U.S. Pat. No. 5,026,798, Example C, incorporated herein by reference), in 50 mL diethyl ether. After stirring overnight, 1.5 mL methanol was added. Solvents were removed under vacuum and the residue extracted with dichloromethane. The extracts were filtered through diatomaceous earth, 10 mL heptane was added, and the solution then slowly concentrated on a rotary evaporator. After nearly all the dichloromethane had been removed, the product separated as a white microcrystalline solid that was isolated by filtration. The yield was 3.9 g (63%), mp 153–154° C. Spectroscopic and chemical analysis confirmed the identity of the desired compound.

Example 7

{CPA-$SiMe_2$-flu}$ZrCl_2$ (designated Example 18R, below)

$Li_2${CPA-$SiMe_2$-flu} was prepared by treating a solution of 1.65 g CPA-$SiMe_2$-flu (prepared as in Example 6) in 40 mL diethyl ether with 3.2 mL 2.5M butyllithium in hexane. After stirring overnight, solvents were removed on a vacuum line. Zirconium tetrachloride (0.93 g) was added and the mixture cooled to –79° C. with a dry ice-acetone bath. Dichloromethane, 75 mL, precooled to –78° C., was added and the reaction mixture was vigorously stirred overnight as the cooling bath warmed to room temperature. The red solid phase was separated and extracted with five 100 mL portions of dichloromethane. The filtered extracts were evaporated and the residue was washed with hexanes to give 0.48 g (24%) red microcrystals. Spectroscopic and chemical analysis confirmed the identity of the desired compound.

Example 8

Copolymerization of Propylene and 1-Octene

A catalyst prepared by stirring 0.018 g {CPA-SiMe$_2$-flu}ZrCl$_2$ (Example 7) and 21 mL methylaluminoxane solution was added to a mixture of 48 g 1-octene and 1816 g propylene which were contained in the reactor as described in Example 4. The polymerization temperature was maintained between 15° and 20° C. for 4 h, after which the reaction was terminated. The copolymer product weighed 950 g and contained 1.1 wt. % (0.4 mole %) octene. $^{13}$C NMR analysis showed 4.6% mrnmm, 8.6% mmmr, 6.2% rmmr, 12.6% mmrr, 19.1% rmmr/mmrm, 9.5% rmrm, 20.6% rrrr, 14.2% mrrr, 4.6% mrrm, 19.4% mm, 41.2% mr and 39.4% rr. Spectroscopic and chemical analysis confirmed the identity of the desired product.

Copolymers of propylene and ethylene, butene, hexene or mixtures thereof can be prepared as in this Example by substituting one or more of them for the octene used herein.

Example 9

Dihydrocyclopentaphehenanthrene, H$_2$CPA

A mixture of 2 g cyclopentaphenanthrene, 0.2 g 10% palladium on carbon and 50 mL toluene was stirred untder hydrogen (69 kPa) until hydrogen uptake ceased, about 48 h. Catalyst was removed by filtration through diatomaceous earth and the filtrate evaporated. The crude product remaining weighed 1.97 g. It was further purified by recrystallization from heptane at −40° C. to give 1.8 g colorless plates. Spectroscopic and chemical analysis confirmed the identity of the desired compound.

Example 10

{H$_2$CPA-SiMe$_2$-flu}ZrCl$_2$(designated 18T in Table 1, below)

H$_2$CPA-SiMe$_2$-flu was prepared from dihydrocyclopentaphenanthrene (Example 9) and 9-flu-SiMe$_2$Cl by the method described in Example 6. The crude product was recrystallized by slow rotary evaporation from solution in dichloromethane-acetone. The yield of white powdery solid, mp. 155–156° C., was 58%. Spectroscopic and chemical analysis confirmed the identity of the desired compound.

This compound was converted to the metallocene catalyst {H$_2$CPA-SiMe$_2$-flu}ZrCl$_2$ by the method described in Example 3. The mass spectrum showed a cluster of molecular ions having the correct distribution of Cl and Zr isotopomers.

Example 11

{2-Methylbenzindene-C$_2$H$_4$-flu}ZrCl$_2$ (designated 18D in Table 1, below)

A mixture of isomeric 2-methylbenzindenes was prepared by the method described by Stehling et al., *Orgtinometallics*, 13, 964 (1994). A solution of 3.6 g of this material was dissolved in 90 mL diethyl ether and converted to the lithium salt by dropwise addition of 8 mL 2.5M butyllithium in hexane. This was added to 20 mmole flu-CH$_2$—CH$_2$—OSO$_2$CF$_3$ (Example 1) in 100 mL toluene. After stirring overnight, the reaction mixture was filtered and evaporated. The residual gum was extracted with 300 mL boiling heptane. The extract was cooled to −5° C. and the yellow solids which separated were collected on a filter. Further purification of the solids was carried out by chromatography on an 20.3×3.8 cm silica gel column, eluting with 1:1 (v/v) toluene - heptane. Evaporation of the eluate gave 3.6 g crude methylbenzindene-C$_2$H$_4$-flu as an amber resin.

A 3.48 g quantity of this crude adduct was dissolved in 50 mL ether and treated with 7.5 mL 2.5M butyllithium in hexane. After stirring overnight, most of the liquid phase was removed with a hypodermic syringe. The residue was dried by pumping on a vacuum line then washed with hexane, after which 50 mL hexane and 0.98 g zirconium tetrachloride were added. After stirring for 48 h, the reaction mixture was filtered and the solids extracted with five 50 mL portions of dichloromethane. The filtered extracts were evaporated and washed with hexane to leave 0.73 g of product as a bright orange powder. Spectroscopic and chemical analysis confirmed the identity of the desired compound.

Example 12

Propylene Polymerization with {2-Methylbenzindene-C$_2$H$_4$-flu}ZrCl$_2$

A catalyst solution was prepared by stirring 0.04 g of the metallocene catalyst obtained in Example 11 with 15 mL methylaluminoxane solution. The catalyst solution was injected into 1816 g propylene held at 8° C. After 40 min, the temperature inside the reactor had risen to 26° C. and maintained at that temperature for 4.5 h, after which the polymerization reaction was terminated. The yield of polymer product was 1534 g. $^{13}$C NMR analysis gave 30.9% mmmm, 14.2% mmmr, 4.9% rmmr, 16.2% mrr, 8.3% rmrr/mmrrn, 3.7% rmirm, 7.1% rrrr, 7.8% mirr, 7.8% mrrm, 50.0% mm, 28.2% mr and 21.8% rr. Spectroscopic and chemical analysis confirmed the identity of the desired product. The polymer was extracted with hot heptane (at about 95° C.) in a Soxhlet apparatus. No material remained unextracted. Recovery was about 95% with 5% attributed to mechanical losses. The $^{13}$C NMR spectrum of the recovered polymer matched that of the starting material within experimental error, indicating that an insoluble, crystalline phase was not present.

Example 13

{H$_2$CPA-C$_2$H$_4$-flu}ZrCl$_2$(designated 18S in Table 1, below)

A slurry of Li(H$_2$CPA) was prepared by treating 15 mmole (2.88 g) dihydrocyclopentaphenanthrene (Example 9) in 50 mL diethyl ether with 6 mL 2.5M n-butyllithium in hexane. Toluene, 50 rnL, was added to reduce the viscosity. This slurry was added to 15 mmole flu-CH$_2$—CH$_2$—OSO$_2$CF$_3$ in 75 mL toluene (Example 2). The desired adduct, H$_2$CPA-C$_2$H$_4$-flu was obtained as colorless crystals. After recrystallization from CH$_2$Cl$_2$-acetone 50% yield was obtained. Spectroscopic and chemical analysis confirmed the identity of the desired compound.

The adduct was converted to the metallocene {H$_2$CPA-C$_2$H$_4$-flu}ZrCl$_2$ by the method described in Example 3. The yield of carmine colored microcrystals was 50%. Spectroscopic and chemical analysis confirmed the identity of the desired compound.

Example 14

Propylene Polymerization using {H$_2$CPA-C$_2$H$_4$-flu}ZrCl$_2$

A. Polymerization at 68° C. A catalyst prepared by stirring 0.022 g {H$_2$CPA-C$_2$H$_4$-flu}ZrCl$_2$ with 15 ml, methylaluminoxane solution was aidded to 1816 g propylene at 1° C., according to the method described in Example 4. Within 7 min, the temperature rose to 23° C. and circulation of coolant was started. I' he temperature continued to rise until it reached 68° C., then declined slowly. After about 3 h, the reactor was vented and 1435 g colorless, tacky, elastic polypropylene was removed. $^{13}$C NMR showed 2.4% mmmm, 6.0% mmmr, 5.7% rmmr, 12.2% mmrr, 20.8% rmrr/mmrm, 10.7% rmrm, 20.8% rrrr, 15.8% mrrr, 5.7% mrrm, 14.0% mm, 43.8% mr and 42.3% rr.

B. Polymerization at 28° C. The polymerization reaction in Run A was repeated but the amount of metallocene used was reduced to 0.008 g. The reaction temperature was kept at about 28° C. by circulation of coolant through the jacket surrounding the reactor. After 3 hr, unreacted propylene was vented and 1748 g nontacky, elastic polymer was removed from the reactor. $^{13}$C NMR analysis showed 0.9% mmmm, 3.3% mmmr, 6.0% rmmr, 11.4% mmrr, 12.3% rmrr/mmrm, 4.8% rmrm, 42.0% rrrr, 17.1% mrrr, 2.2% mrrm, 10.2% mm, 28.5% mr and 61.3% rr. Spectroscopic and chemical analysis confirmed the identity of the desired product.

Example 15

{CPA-C$_2$H$_4$-flu}HfCl$_2$

The ligand CPA-C$_2$H$_4$-flu was obtained as colorless needles from toluene-heptane, m.p. 225–227° C., in 51% yield by the reaction of the lithium salt of cyclopentaphenanthrene with flu-C$_2$H$_4$-OSO$_2$CF$_3$ according to the method described in Example 2. Spectroscopic and chemical analysis confirmed the identity of the desired compound.

A 1.0 g quantity of the above adduct, suspended in 50 mL ether, was treated with 2.1 mL 2.5M butyllithium in hexane. After 12 h, solvents were removed on a vacuum line. Solid hafnium tetrachloride, 0.83 g and 50 mL hexane were added. The reaction mixture was stirred vigorously for 24 h. The finely divided, crude, orange product was isolated by centrifugation and washed with hexane then toluene and vacuum dried. The yield was 0.8 g. The metallocene was used without further purification in subsequent polymerization reactions. Spectroscopic and chemical analysis confirmed the identity of the desired compound.

Example 16

Propylene Polymerization using {CPA-C$_2$H$_4$-flu}HfCl$_2$

A 0.025 g quantity of the metallocene obtained in Example 15 was stirred for 38 min with 18 mL methylaluminoxane solution. This mixture was added to 1816 g propylene held at 0° C. The reactor was allowed to warm to room temperature, then vented and opened. The polymer thus obtained, 43 g, was removed. $^{13}$C NMR analysis gave 4.4% mmmm, 6.3% mmmr, 5.7% rmmr, 12.3% mmrr, 15.9% rmrr/mmrm, 8.4% rmrm, 27.7% rrrr, 14.1% mrrr, 5.2% mrrm, 16.4% mm, 36.6% mr and 47.0% rr. Spectroscopic and chemical analysis confirmed the identity of the desired product. GPC analysis gave $M_w$ 9.5E5, $M_n$ 3.2E5, and $M_w/M_n$ 2.84.

Example 17

{CPA-C$_2$H$_4$-flu}ZrCl$_2$ (designated 18Q in Table 1, below)

To a suspension of 1.91 g CPA-C$_2$H$_4$-flu (Example 15) in 70 mL diethyl ether was slowly added 4 mL 2.5 M n-butyllithium in hexane. An orange crystalline solid separated. The reaction mixture was stirred overnight at 23° C., after which solvents were removed in a vacuum line. The reaction flask containing the solid dilithium salt thus obtained was cooled in a acetone-dry ice bath, and 1.17 g solid ZrCl$_2$ was added, followed by 70 mL dichloromethane that had been precooled to –78° C. The reaction mixture was stirred overnight as the cold bath warmed to 23° C. The solid phase was isolated by centrifugation, then washed successively with hexane, absolute ethanol, and hexane. The bright red solid product, dried under vacuum, weighed 1.53 g (57%). Spectroscopic and chemical analysis confirmed the identity of the desired compound.

Example 18

Propylene Polymerization Reactions

Propylene was polymerized at 25±10° C. by the method described in Example 4. A 20±10 mg quantity of metallocene was employed ; the exact amount was chosen so as to enable maintenance of temperature and prevent too vigorous a reaction. These catalysts, their A.P. values, and the S.I. of the product polymers, are summarized in Table 1, below. Table 2, below summarizes stereochemical and molecular weight data for some polypropylenes prepared with Class A catalysts. Table 2 also includes results from polymerization reactions carried out at higher and lower temperatures. This has been denoted by subscripts (i.e. 1 or 2) indicating reaction at different temperatures.

Table 3, below, presents stereochemical analyses of polypropylenes prepared using Class B catalysts. This Table illustrates how the stereochemical preference of these metallocenes, i.e. whether a syndio- or isotactic-rich polymer is formed, varies unpredictably with the structural details of the catalyst. The data also show brinlo(lail molecular weight distributions and peak molecular weight, $M_p$, of each of the two distributions which are given in the last two columns in Table 3.

TABLE 1

| Example | | A.P. | S.I. | rr/mm |
|---|---|---|---|---|
| 18A* | (fluorenyl-C$_2$H$_4$-fluorenyl)ZrCl$_2$ | 1.00 | 1.13 | 23/26 |
| 18B | (fluorenyl-C$_2$H$_4$-3-phenylindenyl)ZrCl$_2$ | 1.16 | 1.50 | 36/24 |
| 18C | (fluorenyl-C$_2$H$_4$-2-phenylindenyl)ZrCl$_2$ | 1.16 | 2.73 | 22/60 |
| 18D | (fluorenyl-C$_2$H$_4$-2-methyl-4,5-benzoindenyl)ZrCl$_2$ | 1.22 | 2.27 | 22/50 |
| 18E* | (fluorenyl-CMe$_2$-cyclopentadienyl)ZrCl$_2$ | 2.09 | 27.30 | 82/3 |
| 18F | (fluorenyl-C$_2$H$_4$-3,4-benzofluorenyl)ZrCl$_2$ | 1.18 | 1.33 | 24/32 |
| 18G | (fluorenyl-C$_2$H$_4$-4-phenylfluorenyl)ZrCl$_2$ | 1.44 | 1.68 | 22/37 |
| 18H* | (fluorenyl-C$_2$H$_4$-4-(1-naphthyl)-2,7-di-t-butylfluorenyl)ZrCl$_2$ | 1.70 | 13.30 | 6/80 |

TABLE 1-continued

| Example | | A.P. | S.I. | rr/mm |
|---|---|---|---|---|
| 18I | (fluorenyl-$C_2H_4$-3-methylindenyl)$ZrCl_2$ | 1.16 | 1.12 | 29/26 |
| 18J | (fluorenyl-$C_2H_4$-3-trimethylsilylindenyl)$ZrCl_2$ | 1.30 | 2.19 | 21/46 |
| 18K | (fluorenyl-$C_2H_4$-3-trimethylsilylindenyl)$HfCl_2$ | 1.30 | 1.44 | 25/36 |
| 18L* | (fluorenyl-$C_2H_4$-2,7-di-para-tolylfluorenyl)$ZrCl_2$ | 1.00 | 1.08 | 28/26 |
| 18M* | (fluorenyl-$C_2H_4$-2,7-di-tert-butylfluorenyl)$ZrCl_2$ | 1.00 | 1.26 | 23/29 |
| 18N | (fluorenyl-$C_2H_4$-indenyl)$ZrCl_2$ | 1.35 | 1.65 | 43/26 |
| 18O* | (fluorenyl-$CH_2SiMe_2$-fluorenyl)$ZrCl_2$ | 1.00 | 1.04 | 25/24 |
| 18P* | (fluorenyl-$SiMe_2$-fluorenyl)$ZrCl_2$ | 1.00 | 1.31 | 29/22 |
| 18Q | (fluorenyl-$C_2H_4$-cyclopentaphenanthryl)$ZrCl_2$ | 1.08 | 1.84 | 35/19 |
| 18R | (fluorenyl-$SiMe_2$-cyclopentaphenanthryl)$ZrCl_2$ | 1.08 | 2.47 | 42/17 |
| 18S | (fluorenyl-$C_2H_4$-4,5-dihydrocyclopentaphenanthryl)$ZrCl_2$ | 1.13 | 6.10 | 61/10 |
| 18T | (fluorenyl-$SiMe_2$-4,5-dihydrocyclopentaphenanthryl)$ZrCl_2$ | 1.13 | 5.90 | 59/0 |
| 18U | (fluorenyl-$SiPh_2$-4,5-dihydrocyclopentaphenanthryl)$ZrCl_2$ | 1.13 | 5.09 | 56/11 |
| 18V | (perhydrocyclopentaphenanthryl-$C_2H_4$-perhydrofluorenyl)$ZrCl_2$ | 1.10 | 3.92 | 51/13 |
| 18W* | (fluorenyl-$C_2H_4$-4-methylfluorenyl)$ZrCl_2$ | 1.11 | 1.03 | 38/37 |
| 18X | (cyclopentaphenanthryl-$SiMe_2$-indenyl)$ZrCl_2$ | 1.46 | 6.36 | 11/70 |
| 18Y | (3,4-Dimethylfluorenyl-$SiMe_2$-3,4-dimethylfluorenyl)$ZrCl_2$ | 1.00 | 1.28 | 32/25 |
| 18Z* | (fluorenyl-$SiMe_2$-indenyl)$ZrCl_2$ | 1.35 | 1.88 | 24/45 |
| 18AA | (fluorenyl-$SiPh_2$-indenyl)$ZrCl_2$ | 1.35 | 1.23 | 37/30 |

*Comparative Example (both catalyst and polypropylene known in the art)

TABLE 2

Polypropylenes Prepared with Some Type A Catalysts

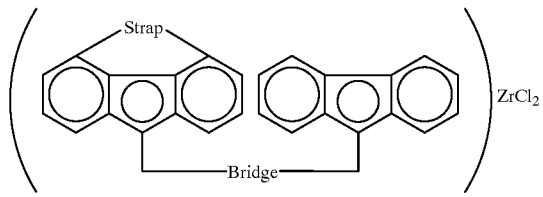

| Example | Strap | Bridge | Rx Temp | % rrrr | % rr/% mm | $M_w/M_n$ | PD* |
|---|---|---|---|---|---|---|---|
| 18$Q_1$ | —CH=CH— | $CH_2$—$CH_2$ | −20 | 21 | 42/15 | 7.2E5/4.2E5 | 1.71 |
| 18$Q_2$ | —CH=CH— | $CH_2$—$CH_2$ | +10 | 16 | 35/19 | 6.3E5/3.3E5 | 1.3 |
| 18$T_1$ | $CH_2$—$CH_2$ | $SiMe_2$ | +25 | 40 | 59/10 | 6.6E5/4.1E5 | 1.6 |
| 18$T_2$ | $CH_2$—$CH_2$ | $SiMe_2$ | +50 | 34 | 56/11 | 2.9E5/1.1E5 | 2.6 |
| 18R | —CH=CH— | $SiMe_2$ | +15 | 25 | 42/17 | 1.4E6/4.9E5 | 2.85 |
| 18U | $CH_2$—$CH_2$ | $SiPh_2$ | +25 | 33 | 57/12 | 1.4E6/5.8E5 | 2.4 |
| 18$S_1$ | $CH_2$—$CH_2$ | $CH_2$—$CH_2$ | +65 | 21 | 42/14 | 8.0E4/1.9E4 | 4.2 |
| 18$S_2$ | $CH_2$—$CH_2$ | $CH_2$—$CH_2$ | +28 | 42 | 61/10 | 7.1E5/2.5E5 | 2.84 |

*PD means polydispersity, i.e., $M_w/M_n$.

TABLE 3

Polypropylenes Prepared with Some Type B Catalysts

[Structure: fluorenyl-C$_2$H$_4$-cyclopentaphenanthryl MCl$_2$ with R substituent]

| Ex. | R | M | AP | S.I. | mm:mr:rr | M$_p$ (%) | M$_p$ (%) |
|---|---|---|---|---|---|---|---|
| 18N* | H | Zr | 1.35 | 1.65 | 26:31:43 | 7.1E4 (20) | 8.2E4 (80) |
| 18B | 3-Ph | Zr | 1.16 | 1.50 | 24:41:36 | 6.2E5 (69) | 1.3E5 (11) |
| 18J | 3-SiMe$_3$ | Zr | 1.30 | 2.19 | 46:33:21 | 4.3E5 (50) | 8.9E4 (50) |
| 18K | 3-SiMe$_3$ | Hf | 1.30 | 1.44 | 36:39:25 | 5.1E5 (50) | 8.1E4 (50) |
| 18I | 3-CH$_3$ | Zr | 1.16 | 1.12 | 26:45:29 | 6.3E5 (78) | 1.6E5 (18) |
| 18D | 2-Me-4,5-benzo | Zr | 1.22 | 2.27 | 50:28:22 | 6.2E5 (100) | † |

†sample had single peak

[Structure: fluorenyl-bridge-cyclopentaphenanthryl ZrCl$_2$]

| Ex. | Bridge | mm:mr:rr | A.P. | S.I. | M$_p$ (%) | M$_p$ (%) |
|---|---|---|---|---|---|---|
| 18N* | C$_2$H$_4$ | 26:31:43 | 1.35 | 1.65 | 7.5E5 (20) | 8.2E4 (80) |
| 18Z* | SiMe$_2$ | 45:32:24 | 1.35 | 1.88 | 3.5E5 (15) | 9.6E4 (85) |
| 18AA | SiPh$_2$ | 30:33:37 | 1.35 | 1.23 | 5.8E5 (76) | 9.6E4 (24) |

*Catalyst is known in the art

Example 19

Polypropylene Properties

Polypropylene was prepared by the method described in Example 4, using catalyst 18Q$_1$ ((fluorenyl-C$_2$H$_4$-cyclopentaphenanthryl)ZrCl$_2$), except that the reaction temperature was kept at −20° C. As shown in Table 2, the S.I. for the resulting polymer was 42/15=2.8, indicating that the lower-temperature reaction (compared to the polymer resulting from the use of catalyst 18Q$_2$ (reaction temperature=+ 10° C., S.I.=1.84) produced a polypropylene having a higher percentage of syndiotacticity.

A sample of the low-temperature polymer, from catalyst 18Q$_1$ was pressed into a thin film using a Carver hydraulic press (Fred S. Carver, Inc., Model 2699, Wabash, IN) by pressing at 170° C. for two minutes. When cooled to 23° C., two samples of the film were subjected to Dynamic Mechanical Analysis at 1 Hz using a Rheometrics Model RSAII rheometer (Rheometric Scientific, Piscataway, N.J.) at −60° C. and +250° C., respectively, in order to avoid thermal equilibrium or annealing effects on transitions. Thermal expansion of the sample was compensated for by adjustment of the dynamic oscillatory strain amplitude.

FIG. 4 shows the tensile storage modulus (Trace A), the loss modulus (Trace B), and the loss tangent or tan delta (Trace C), of the sample. As can be seen in FIG. 4, Trace A, the polypropylene of the invention, from catalyst 18Q$_1$, exhibited a sharp drop in elastic modulus between −3° and +8° C., followed by a surprising essentially flat tracing up to about 175° C., more particularly between +8° and +174° C., a property that is unprecedented for a polypropylene having no measurable gross crystallinity by WAXS or detectable melting point by DSC.

Trace B shows the loss modulus for this sample, which is a measurement of the ability of the material to dissipate heat when deformed. The slight rise in loss modulus with temperature is an indication of loss of structural order as the temperature increases, at about 180° C., an abrupt change in slope of Trace B is indicative of a physical change, such as melting. Trace C shows the ratio of loss modulus to tensile storage modulus (E″/E′), also known as tan delta, for the sample, and is wholly derived from the two previous traces.

The tensile storage modulus shown in FIG. 4 corresponding to the elastic flat plateau allows calculation of an entanglement molecular weight ($\overline{M}_e$) for the polypropylene of this Example of 3620 g/mole, a value less than that predicted for pure atactic polypropylene, i.e., 4650 g/mole (Z. Xu, et al., Advances in Polymer Science, Vol. 120, Springer Verlag, Berlin (1995), pp. 1–50).

A sample of the polypropylene of the invention was further annealed at 150° C. for 60 minutes, then slowly cooled to 23° C. at 1° C./minute prior DMA analysis. The DMA analysis indicated that the polymer behaved like an uncrosslinked polypropylene, that is, fine structure that may contribute to a plateau in the elastic modulus was prevented from forming by the slow cooling process. This shows that the source of elastic behavior over an extended temperature range was not due to the relatively high molecular weight of the polypropylene alone, but was reasonably attributed to the nanocrystallinity of the sample before annealing.

This experiment shows that polypropylene prepared, for example, using catalysts 18Q, 18Q$_1$, 18R, 18S, 18T, 18U, of the invention exhibited physical properties that have not been described previously, that is, rubbery elastic behavior over an extended temperature range, without evidence of gross crystallinity. Without wishing to be bound by theory, it is postulated that this behavior, coupled with the calculated low entanglement molecular weight, is indicative of a near perfect infinite network structure generated by extremely fine scale crystallinity.

Example 20

Time Dependence of Modulus for Polypropylene

Polypropylene was prepared according to the method of Example 4 using catalyst $18T_1$ ((fluorenyl-dimethylsilyl-4,5-dihydrocylopentaphenanthryl)$ZrCl_2$; polymerization at 25° C., per Table 3). A melting point of 48° C. was found via Modulated Differential Scanning Calorimetry (MDSC) methods (Model 2980, TA Instruments, Inc., New Castle Del.). Analysis by WAXS methods established the presence of crystallinity in the sample by comparison with spectra of commercially-available polypropylene: Rexene™ D-100 (isotactic polypropylene from metallocene catalyst, Rexene Corp., Dallas, Tex.); Exxon™ 3505 (isotactic polypropylene from Ziegler-Natta catalyst, Exxon Chemicals Co., Houston, Tex.).

A film sample was prepared by pressing the polymer in a Carver press at 176° C., then allowing the film to cool to 23° C. The tensile storage modulus of a portion of the film was then determined over a lengthy time period by Dynamic Mechanical Analysis using a Rheometrics RSA II analyzer. Results of the analysis are shown in Table 4, below.

TABLE 4

Modulus as a Function of Time at 23° C.

| Time after preparation, hours | Tensile Storage Modulus, MPa | Loss Tangent |
|---|---|---|
| 0.5 | 2.23 | 0.16 |
| 2.5 | 2.68 | 0.15 |
| 4.5 | 4.36 | 0.15 |
| 23 | 3.14 | 0.12 |
| 100 | 10.2 | 0.14 |
| 120 | 10.3 | 0.14 |

The data of Table 4 show surprising polypropylene behavior, that is, an increase in tensile storage modulus by a factor of 5 over a 5-day period while the loss tangent remained unchanged. Measurement of tensile storage modulus of the sample after aging for 28 days, using a Rheometrics RSAII instrument, revealed the data shown in FIG. 5, which clearly shows the newly-developed shoulder in the trace between about 15° and 45° C., corresponding to the increase in tensile modulus shown in Table 4. Using this first "step" modulus, an entanglement molecular weight of 545 was calculated, indicating a higher degree of structural order than shown for the final, higher temperature equilibrium tensile modulus plateau to 170° C. A higher molecular weight for the aged sample can be indicative of a tightly crosslinked polymer.

In a related study, a portion of the same polypropylene (from catalyst 188T,) was annealed at 170° C. for 7–10 minutes under nitrogen, then cooled at 10° C./minute to simulate a supercooling process that wipes out previous heating and cooling history without thermal degradation of the sample. The growth in tensile modulus for the annealed material was followed at 45° C. for 70 hours, during which time the tensile modulus increased from 6.5 to 30 MPa. MDSC analysis of the aged sample showed a melt endotherm at 48° C., and a crystallinity of 24% was estimated from the melting enthalpy. WAXS and MDSC data was consistent with syndiotactic crystallinity in the aged material.

The ability of polypropylenes of the invention to organize over time was demonstrated for polymers prepared from catalysts 18T (polymerization at 50° C.), 18S (polymerization at 65° C.), and 18Q, as well as from the hafnium metallocene catalyst prepared in Example 5.

Example 21

Permanent Set Properties of Polypropylenes

The two polypropylenes prepared as described in Examples 19 and 20 (i.e., polypropylene from catalyst $18Q_1$ and $18T_1$, Table 2) were further characterized by their permanent set properties, by methods described in the art, in comparison to commercially-available rubbery polypropylene (Rexene™ D-100). In these characterizations, "permanent set" of a given percentage means that, after stretching the material at a specified percent elongation for a specified time, the material equilibrates at a length longer than its original length by the given percentage. Thus, a permanent set of 10% means that the final length of the material was 10% longer than its original length, and a permanent set of "nil" means that the final length was the same as the original length. The data for the characterizations is shown in Table 5, below. Methods described in U.S. Pat. No. 5,549,080, Example 33, which employed an initial 300% elongation, and European Patent Application No. 707,016, p. 19, which employed an initial 100% elongation, as well as an initial elongation of 200%, were used.

Data in Table 5, below, show that polypropylenes of the invention exhibit less permanent set, i.e., more elasticity, by any of three methods, than a commercial "elastic" polypropylene. The 75% permanent set in the commercial material can be interpreted as plastic deformation of crystallites, which was not observed in polypropylenes of the present invention. Elasticity is an important and useful characteristic in polymers used, e.g., for adhesives.

TABLE 5

Permanent Set in Polypropylenes
Sample % Permanent Set

| Method | $18\text{-}Q_1$ | 18T | Rexene D-100 (Comparative) |
|---|---|---|---|
| A: Immediate Test | 0 | 5.0 | 17.5 |
| A: 10 Minutes Rest and Test | 0 | 2.5 | 17.5 |
| B: Immediate Test | 2.5 | 10.0 | 85.0 |
| B: 10 Minutes Rest and Test | 2.5 | 7.5 | 75.0 |
| C: Immediate Test | 0 | 7.5 | 50.0 |
| C: 10 Minute Rest and Test | 0 | 5.0 | 42.5 |

Method A: EP 707016, p. 19 Sample was stretched to 100% extension; held for one minute. Test set evaluated immediately after relaxation and 10 minutes after relaxation
Method B: U.S. Pat. No. 5,594,080 Sample was stretched to 300% and allowed to relax immediately. Evaluated immediately after relaxation and 10 minutes after relaxation
Method C: Data were collected at 200% extension.

Example 22

Tack and Adhesion of Polypropylenes

Polymers prepared by the method described in Example 4 from catalysts $18S_1$ and $18S_2$ (Table 2), that is, the same catalyst but polymerization is carried out at +65° C. (catalyst $18S_1$) and at +28° C. (catalyst $18S_2$) were isolated, then blended as described below.

The polypropylene from catalyst $18S_1$ (hereinafter referred to as 'polymer A') was a tacky, film forming material having a weight average molecular weight of 80,000 and an S.I. of 3.0. The polypropylene from catalyst 18S$_2$ (hereinafter referred to as 'polymer B') had a weight average molecular weight of 710,000 and an S.I. of 6.1. As noted in Example 14, polymer B was found to have twice as many rrrr pentads as polymer A. Blends of 70:30 A:B and 70:30 B:A were prepared and coated at two thicknesses onto poly(butylene terephthalate) (PBT) that had been sputter plasma etched to provide increased adhesiveness to coatings. Shear adhesion data for the four formulations are shown in Table 6, below, for a 1 Kg load on a 1 inch×½ inch (2.5 cm×1.3 cm) tape.

Blends were prepared in a Haake-Brabender mixing apparatus (C. W. Brabender Co., South Hackensack, N.J.) at 210° C., then fused to the PBT using a Carver press at 177° C. and 575 kPa for 3 minutes. Shear adhesion tests were performed according to ASTM Method D3654M-88. The data of Table 6 show that moderate to good pressure sensitive adhesives were formed from polypropylenes of the invention, and that failure-resistant bonding occurred when the majority of the polymer had a higher weight average molecular weight. Polypropylenes of the invention were blended with numerous other polymers, such as crystalline polypropylene(s), tacky poly-1-hexene and poly-1-octene to tailor the adhesive performance of the mixtures as well as the rheology of the mixtures (i.e., hot-melt type adhesives were prepared from polypropylene and/or the mixtures noted above).

TABLE 6

Shear Adhesion
PSTC Test Method

| Sample | Adhesive Blend Composition Polymer S$_1$ | Polymer S$_2$ | Adhesive Thickness (Substrate, PBT)* | Shear Adhesion 23° C. Minutes to Failure; 2.5 × 1.3 cm tape 1 Kg Load |
|---|---|---|---|---|
| 22A | 70 | 30 | 0.0035 | 407 |
| 22B | 30 | 70 | 0.0035 | 1895 |
| 22C | 70 | 30 | 0.0015 | 200 (partial cohesive failure) |
| 22D | 30 | 70 | 0.0015 | 3380 |

*Sputter plasma etched polybutyleneterephthalate

Example 23

Polypropylene Physical Properties Based On Catalysts Having C$_s$ Symmetry

A synopsis of physical properties observed for polypropylenes of the invention, prepared using catalysts having C$_s$ symmetry, also referred to as Type A catalysts, is presented in Table 7, below. Samples were prepared by pressing the polypropylene into a film in a Carver press at 175° C., then allowing the film to cool to 23° C. over a short period of time. In the Table, Tensional Modulus values were obtained using a Rheometrics RSA II instrument. Extrusion viscosity values were obtained at 230° C. (except for sample 23G, at 175° C.), using a 1 mm diameter capillary having a length/diameter ratio of 50:1 on a Series 4200 Instron Capillary Rheometer (Instron Corp., Canton, Mass.), Tensile strength and elongation at break values were obtained using an Material Test System Model 880 servohydraulic tester (MTS Systems Corp., Minneapolis, Minn.) at a crosshead speed of 30.5 cm/minute. Inelasticity figures refer to a protocol of stretching a sample to 10% (ASTM D1774-90 using MTS Model 880 machine, also) and 15%, respectively, of its original length, holding for 3 minutes at 23° C., then releasing tension and allowing the sample to recover to an equilibrium length. The figure reported is the percent permanent elongation of the sample after release of tension.

Data shown in Table 7, below, support the observation that polypropylenes of the invention are highly elastic, having tensile strengths below 8.90 MPa with no observable yield point. The lack of a yield point indicated lack of measurable gross crystalline structure, further supporting the conclusion that these elastic polymers possessed a near perfect infinite network structure generated by nanocrystals of polypropylene.

TABLE 7

Type A Catalysts: Synopsis of Physical Properties of Polypropylene

| Ex. | Catalyst (Table 2) | Tensile Strength MPa | Elongation at Break % | Tensional Modulus, Mpa 23° C. | 150° C. | Inelasticity 10% Strain | 15% Strain | Extrusion Viscosity @ 10 sec − 1, Pa-sec |
|---|---|---|---|---|---|---|---|---|
| 23A | 18Q$_1$ | 2.14 | 545 | 2.21 | 1.69 | 4.5 | 0 | 1.1 × 10$^4$ |
| 23B | 18Q$_2$ | 1.45 | 1100 | 1.76 | 0.90 | 0 | 2.7 | 1.0 × 10$^4$ |
| 23C | 18T$_1$ | 2.21 | 710 | 13.0 | 2.21 | 0 | 2.8 | 1.0 × 10$^4$ |
| 23D | 18T$_2$ | 3.04 | 1700 | 2.41 | 0.23 | * | * | 6 × 10$^3$ |
| 23E | 18R | 0.59 | 1200 | 2.65 | 1.93 | * | * | 1 × 10$^4$ |
| 23F | 18U | 2.55 | 345 | 1.04 | * | * | * | 1.1 × 10$^4$ |
| 23G | 18S$_1$ | ~0.72 | >1000 | ** | * | * | * | 2.1 × 10$^2$ (175° C.) |
| 23H | 18S$_2$ | 8.90 | ≧1000 | 8.14 | 0.31 | * | * | 3.5 × 10$^3$ |

* not measured
** not measurable in tension mode

Example 24

Polypropylene Physical Properties Based On Catalysts Having $C_1$ Symmetry

A synopsis of physical properties observed for polypropylenes of the invention, prepared using catalysts having $C_1$ symmetry, also referred to as Type B catalysts, is presented in Table 8, below. Measurements were taken as described in Example 23. Some of the polypropylenes of Table 8 exhibited very large extensibility (elongated at break), characteristic of polymers that were uncrosslinked or slightly crosslinked or having an irregular structure. In contrast to the data of Table 7 (Type A catalysts), polypropylenes described in Table 8 exhibited a yield point. Generally, polymers prepared using Type B catalysts had lower (peak) molecular weights than those from Type A catalysts, which were reflected in the generally lower extrusion viscosity values of Table 8 vs. Table 7.

The data of Table 8 also show another instance of the influence of catalyst molecular structure on polypropylene properties. Comparing the polymer obtained using catalyst 18B with that obtained using catalyst 18N, a significant decrease in the yield point and tensile strength was noted. The molecular structure of catalyst 18B comprised a large, bulky phenyl group at the 3-position of the indenyl ligand, where it can significantly interact sterically with the incoming propylene monomer, whereas catalyst 18N had only a small hydrogen atom at the 3-position. It is believed that the decrease in the yield point and tensile strength of the polymer prepared using catalyst 18B was due to a decrease in structural order of the polymer, relative to that of the polymer prepared using catalyst 18N.

TABLE 8

Synopsis of Physical Properties of Polypropylenes Made with Class B Catalysts

| Catalyst (Table 1) | Tensile Strength MPa | Elongation at Break % | Yield Point MPa | Tensile Modulus MPa | Shear Viscosity at 10 sec$^{-1}$, Pa-sec |
|---|---|---|---|---|---|
| 18N* | 0.93 @ 5200% | 5200 (no break) | 0.62 | 2.30 | 480 |
| 18D | 0.80 @ 1000% | 1000 (no break) | 0.34 | 9.90 | 3000 |
| 18B | 0.27 @ 2000% | 2000 (no break) | 0.07 | 2.10 | 280 |
| 18I | 0.02 | 550 | 0.45 | 2.10 | 295 |
| 18AA | 0.39 | 985 | 0.14 | 0.34 | 5000 |
| 18J | 2.58 @ 1000% | 1000 (no break) | 1.30 | 7.25 | 1800 |
| 18K | 3.30 | 500 | 1.69 | 7.25 | 4440 |
| Ex 5 | 2.65 | 430 | 1.90 | 14.30 | 8000 |

* catalyst is known in the art

Various modification and alterations of this invention will become apparent to those skilled in the art without departing from the scope and intent of this invention, and it should be understood that this invention is not to be unduly limited to the following illustrative embodiments set forth herein.

We claim:

1. A composition of matter having a formula selected from the group consisting of H{flu—C$_2$H$_4$—H$_2$CPA}H H{flu—C$_2$H4—2—CH$_3$—4,5—benzindene}H H{flu—SiR$_2$—CPA}H H{flu—SiR$_2$—H$_2$CPA}H wherein R is a methyl or phenyl group.

2. A method of making chemical compounds having the formula

H{ligand1—CH$_2$CH$_2$—ligand2}H wherein ligand1 and ligand2 are different and are selected from the group consisting of substituted and unsubstituted cyclopentadienyl, indenyl, fluorenyl, and cyclopentaphenanthrene ring groups, wherein, when present, ring group substituents are selected from the group consisting of
   i) $C_1$–$C_4$ straight-chain or branched alkyl,
   ii) $C_6$–$C_{20}$ aryl,
   iii) $C_7$–$C_{20}$ alkylaryl,
   iv) $C_4$–$C_7$ cycloalkyl
   v) (—CH$_2$—)$_n$ or (—CH=CH—)$_m$ connecting to adjacent or non-adjacent ring carbon atoms in the same ring structure, wherein n is 3, 4, or 5, and m=1,2,3, or 4,
   vi) fused aromatic rings, and
   vii) fused aromatic rings substituted by any one of groups i)–v), comprising the steps:
   1) deprotonating the hydroxyl group of a compound of the type H{ligand1—CH$_2$CH$_2$OH};

2) reacting the deprotonated compound with highly fluorinated alkyl sulfonyl fluoride to obtain a highly fluorinated alkyl sulfonate of the type H{ligand1—CH$_2$CH$_2$—OSO$_2$R$_f$};

wherein R$_f$ is a straight chain, branched, or cyclic alkyl group containing 1 to 20 carbon atoms and optionally O, N, or S heteroatoms, with more than 50% of the H atoms being replaced by fluorine atoms;
   3) condensing the trifluoromethanesulfonate with the conjugate base of a compound of the type ligand2—H.

3. The method according to claim 2 wherein R$_f$ is a perfluorinated alkyl group.

4. The method according to claim 2 wherein said catalyst is {flu—C$_2$H$_4$—ind}ZrCl$_2$.

5. A metallocene catalyst having the formula

{ligand1—bridge—ligand2}MX$_2$ wherein ligand 1 is selected from the group consisting of cyclopentadienyl (Cp), indenyl (ind) and fluorenyl (flu), 4,5-dihydrocyclopentaphenathryl (H$_2$CPA), and cyclopentaphenanthryl (CPA) ring groups,
   wherein ligand 2 is selected from the group consisting of 4,5-dihydrocyclopentaphenathryl (H$_2$CPA), and cyclopentaphenanthryl (CPA) ring groups,
   wherein the ring groups of ligand 1 and ligand 2 can be substituted by groups selected from the group consisting of
   i) $C_1$–$C_4$ straight-chain or branched alkyl,
   ii) $C_6$–$C_{20}$ aryl,
   iii) $C_7$–$C_{20}$ alkylaryl,
   iv) $C_4$–$C_7$ cycloalkyl, v) $(-CH_2-)_n$ wherein n=3, 4, or 5, or $(-CH=CH-)_m$ wherein m is 1, 2, 3, or 4, connecting adjacent or non-adjacent ring carbon atoms in the same structure, vi) fused aromatic rings, and vii) fused aromatic rings substituted by any one of groups i)–iv); bridge is a linking group joining ligand 1 and ligand 2 at C-1 position of Cp and ind ligands or C-9 position of flu and CPA ligands and is selected from the group consisting of i) $<CR^1R^2$
ii) $<SiR^1R^2$
iii) $-CR^1R^2-CR^3R^4-$
iv) $-SiR^1R^2-SiR^3R^4-$
v) $-CR^1R^2-SiR^3R^4-$
vi) $-SiR^1R^2-CR^3R^4-$, wherein $R^1$, $R^2$, $R^3$, and $R^4$ can be same or different and are selected from the group consisting of H, $C_1$–$C_{20}$ straight-chain or branched alkyl, $C_6$–$C_{20}$ aryl, and $C_3$–$C_8$ cycloalkyl;

M is a metal atom selected from the group consisting of Zr, Hf, and Ti, and

X is selected from the group consisting of Cl, Br, I, $C_1$–$C_{20}$ straight-chain or branched alkyl, $C_6$–$C_{20}$ aryl, $C_7$–$C_{20}$ alkaryl, and $C_7$–$C_{20}$ aralkyl.

6. The metallocene catalyst according to claim 5 wherein ligand 2 is:

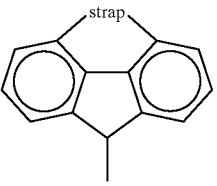

where strap is selected from the group consisting of $-CH=CH-$ and $-CH_2-CH_2-$.

7. The metallocene catalyst according to claim 5 wherein said metallocene catalyst exhibits $C_s$ point group symmetry.

8. The metallocene catalyst according to claim 6 wherein said metallocene catalyst exhibits $C_s$ point group symmetry.

9. The metallocene catalyst according to claim 5 wherein said metallocene catalyst has an asymmetry parameter of at least 1.03 and less than 2.09.

10. The metallocene catalyst according to claim 6 wherein said metallocene catalyst has an asymmetry parameter of at least 1.03 and less than 2.09.

11. The metallocene catalyst according to claim 7 wherein said metallocene catalyst has an asymmetry parameter of at least 1.03 and less than 2.09.

12. The metallocene catalyst according to claim 8 wherein said metallocene catalyst has an asymmetry parameter of at least 1.03 and less than 2.09.

* * * * *

UNITED STATES PATENT AND TRADEMARK OFFICE
CERTIFICATE OF CORRECTION

PATENT NO. : 6,323,151 B1
DATED : November 27, 2001
INVENTOR(S) : Siedle, Allen R.

It is certified that error appears in the above-identified patent and that said Letters Patent is hereby corrected as shown below:

Title page,
Item [56], References Cited, OTHER PUBLICATIONS, "Abstrats" should read -- Abstracts --.

Column 1,
Line 25, "phenylindeniyl" should read -- phenylindenyl --.
Line 25, "liganids" should read -- ligands --.
Line 27, "(1 990)" should read -- (1990) --.
Lines 27 and 28, "macromolecules" should read -- Macromolecules --.
Line 46, "(1 994)" should read -- (1994) --.

Column 2,
Line 26, "mmrnrn" should read -- mmmm --.
Line 37, "Hemi-isofactic" should read -- Hemi-isotactic --.

Column 3,
Line 45, "andic" should read -- and --.
Line 53, "cyclopentadietyl" should read -- cyclopentadienyl --.

Column 4,
Line 16, "1 50 Å," should read -- 150Å --.
Line 37, "hoinotactic" should read -- homotactic --.
Line 67, "rr>rnm" should read -- rr>mm --.

Column 5,
Line 38, "mn" should read -- m --.

Column 6,
Line 47, "4and" should read -- 4 and --.

Column 7,
Line 43, "desircd" should read -- desired --.
Line 44, "andi" should read -- and --.

Column 9,
Line 31, "meclhanical" should read -- mechanical --.
Line 35, "accordilice" should read -- accordance --.
Line 66, "mentionied" should read -- mentioned --.

Column 10,
Line 14, "theiy" should read -- they --.
Line 34, "stricture" should read -- structure --.
Line 51, "inidcnyl" should read -- indenyl --.

UNITED STATES PATENT AND TRADEMARK OFFICE
CERTIFICATE OF CORRECTION

PATENT NO. : 6,323,151 B1
DATED : November 27, 2001
INVENTOR(S) : Siedle, Allen R.

It is certified that error appears in the above-identified patent and that said Letters Patent is hereby corrected as shown below:

Column 11,
Line 54, "sturface" should read -- surface --.

Column 12,
Line 34, "stereoreguzriay" should read -- stereoregularity --.
Line 35, "inldex" should read -- index --.
Line 36, "mm7" should read -- mm --
Line 38, "incrci(sitgly" should read -- increasingly --.
Line 38, "rclaitive" should read -- relative --.
Line 66, "arc" should read -- are --.

Column 13,
Line 22, "PolymerizLtion" should read -- Polymerization --.
Line 25, "inetallocenc" should read -- metallocene --.
Line 29, "poly)ropylenes" should read -- polypropylenes --.

Column 14,
Line 10, "hridcge" should read -- bridge --.
Line 13, "aisymmetry" should read -- asymmetry --.
Line 65, "thie" should read -- the --.

Column 15,
Line 48, "crosslinkining" should read -- crosslinking --.
Line 49, "mielt" should read -- melt --.
Line 57, "DI1774-90)." should read -- D1774-90). --.

Column 16,
Line 25, "oftotally" should read -- of totally --.

Column 17,
Line 45, "Bemoullian" should read -- Bernoullian --.

Column 18,
Line 6, "mimmm" should read -- mmmm --.
Line 18, "triniodal" should read -- trimodal --.
Line 23, "moleculair" should read -- molecular --.
Line 35, "IThe" should read -- The --.

Column 19,
Line 6, "aluminoxanle" should read -- aluminoxane --.

UNITED STATES PATENT AND TRADEMARK OFFICE
CERTIFICATE OF CORRECTION

PATENT NO. : 6,323,151 B1
DATED : November 27, 2001
INVENTOR(S) : Siedle, Allen R.

It is certified that error appears in the above-identified patent and that said Letters Patent is hereby corrected as shown below:

Column 20,
Line 43, "R." should read -- $R_f$ --.

Column 21,
Line 65, "dichlorobenze,e" should read -- dichlorobenzene --.

Column 22,
Line 7, "IFinnigan" should read -- Finnigan --.
Line 45, "Fleats" should read -- Heats --.
Line 45, "fision" should read -- fusion --.
Line 67, "Alter" should read -- After --.

Column 23,
Line 17, "Tile" should read -- The --.
Line 56, "Ihe" should read -- The --.
Line 60, "ajacket" should read -- a jacket --.

Column 24,
Line 4, "nnrm" should read -- rmrm --.
Line 13, "butyllithiurm" should read -- butyllithium --.
Line 32, "butyllithiuin" should read -- butyllithium --.
Line 33, "hlexaine" should read -- hexane --.

Column 25,
Line 12, "mrnmm" should read -- mmmm --.
Line 26, "untder" should read -- under --.
Line 58, "Orgtinometallics" should read -- Organometallics --.

Column 26,
Line 32, "mmrrn" should read -- mmrm --.
Line 49, "50rnL," should read -- 50mL, --.

Column 27,
Line 1, "aidded" should read -- added --.

Column 28,
Line 50, "brinlo(lail)" should read -- brimodal --.

UNITED STATES PATENT AND TRADEMARK OFFICE
CERTIFICATE OF CORRECTION

PATENT NO.   : 6,323,151 B1
DATED        : November 27, 2001
INVENTOR(S)  : Siedle, Allen R.

It is certified that error appears in the above-identified patent and that said Letters Patent is hereby corrected as shown below:

<u>Column 33,</u>
Line 56, "188T," should read -- 18T, --.

Signed and Sealed this

First Day of July, 2003

JAMES E. ROGAN
*Director of the United States Patent and Trademark Office*